United States Patent
Leblanc et al.

(10) Patent No.: US 6,552,073 B1
(45) Date of Patent: Apr. 22, 2003

(54) COMPOUNDS AND METHODS OF TREATING CELL PROLIFERATIVE DISEASES

(75) Inventors: Véronique Leblanc, Paris (FR); Bertrand Leblond, Rouen (FR); Dominique Melle-Milovanovic, Ivry-sur-Seine (FR); Maria Luz Lopez Rodriguez, Madrid (ES); Alma Viso Beronda, Madrid (ES)

(73) Assignee: Exonhit Therapeutics SA, Paris (FR)

( * ) Notice: Subject to any disclaimer, the term of this patent is extended or adjusted under 35 U.S.C. 154(b) by 0 days.

(21) Appl. No.: 10/085,141

(22) Filed: Mar. 1, 2002

(51) Int. Cl.$^7$ .................. A61K 31/351; C07D 309/10
(52) U.S. Cl. ............... 514/460; 549/417; 549/416; 514/460

(58) Field of Search ............... 549/417, 28; 546/296; 514/460

(56) References Cited

U.S. PATENT DOCUMENTS 4,644,071 A * 2/1987 Masateru et al. ........... 549/417

* cited by examiner

Primary Examiner—Alan L. Rotman
Assistant Examiner—Janet L Coppins
(74) Attorney, Agent, or Firm—Nixon & Vanderhye PC

(57) ABSTRACT

The present invention relates to compounds and their uses, particularly in the pharmaceutical industry. The invention discloses compounds having anti-proliferative activities, as well as methods for treating various diseases associated with abnormal cell proliferation, including cancer, by administering said compounds. It further deals with pharmaceutical compositions comprising said compounds, more particularly useful to treat cancers.

23 Claims, 3 Drawing Sheets

COMPOUNDS AND METHODS OF TREATING CELL PROLIFERATIVE DISEASES

Figure 1:
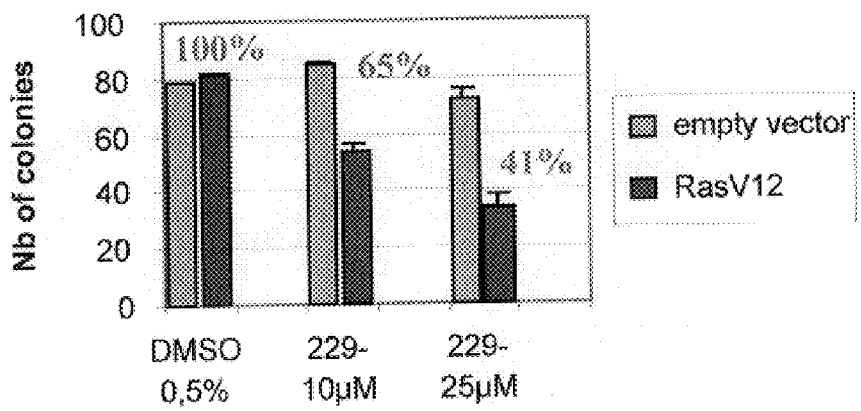

The invention relates to compounds and their uses, particularly in the pharmaceutical industry. The invention discloses compounds having anti-proliferative activities, as well as methods for treating various diseases associated with abnormal cell proliferation, including cancer, by administering said compounds. It further deals with pharmaceutical compositions comprising said compounds, more particularly useful to treat cancers.

Cancer is still one of the leading causes of death in developed countries, as cancer affects all ages, sexes, racial and ethnic groups. According to the American Association for Cancer Research, one out of five deaths in the US is caused by cancer. Worldwide, the most predominant cancer sites are lung (14%), prostate (13%), breast (11%) and colorectal (11%) (data obtained from the Cancer Statistic Branch, NCI).

Cancer rate is increasing in developed countries in spite of falling incidence of several cancers such as prostate cancer (due to detection programs) or lung cancer in men (due to prevention programs). Among the fastest increasing cancer rates are non-Hodgkin's lymphoma cancer and melanoma (3% annual rise) in the US (The Annual Report to the Nation on the Status of Cancer, 1973–1997).

Unlike cancer incidence, cancer deaths have declined in developed countries. This is due in part to better therapy designs but also to prevention programs and better detection of some cancers at an earlier stage.

However, in spite of higher achievements in treatment and prevention of cancers, several improvements are awaited for:
- effective therapies for early stage cancer to reduce relapses,
- alternative therapies for curing tumors refractory to standards therapies,
- alternative therapies for curing metastatic cancers
- less toxic drugs, and
- better delivery systems.

Inhibitors of cell signaling pathways could represent such a new alternative therapy by addressing the first three issues, when used alone or in combination with standard chemotoxic drugs.

There are various receptors, enzymes and effector molecules involved in the biochemical pathways necessary for signal processing in a cell. These include small GTPases, which are monomeric guanine nucleotide-binding proteins of 20–25 kDa molecular mass, which function as molecular switches. They are "on" in the GTP-bound state and "off" in the GDP-bound state. Cycling between the active and inactive forms is controlled by several accessory proteins: the guanine nucleotide exchange factors (GEFs), GTPase-activating proteins (GAPs) and GDP dissociation inhibitors (GDIs). The active GTP-bound GTPases interact with a variety of effectors proteins to produce their cellular effects.

Ras, the first GTPase discovered, gave rise to the Ras super family of GTPases. It is a key regulator of cell growth and is found in mutated oncogenic forms in a large number of human tumors. When specific residues in Ras are mutated, this protein becomes constitutively active (insensitive to GAP action) and causes cell transformation. The Ras oncoproteins are among the most potent mitogenic polypeptides known, and activating mutations of Ras are found in nearly one-third of all human cancers.

The Rho subfamily of GTPases is composed of 3 major subtypes, namely Rho, Rac, and Cdc42, which control actin cytoskeleton in distinct ways. Other major roles for the Rho proteins are the regulation of gene transcription (JNK and p38 mitogen-activated protein kinase, serum response factor, NFkB), cell cycle progression, and adhesion. Several Rho GTPases have been shown to play an important role in cell transformation.

U.S. Pat. No. 4,590,201 discloses compound L651582, a cell signaling inhibitor. This compound inhibits proliferation and inflammation by affecting the biochemical pathways necessary for signal processing in the cell. It is an indirect blocker of the effector enzymes which produce the second messengers necessary to induce growth.

The present invention now relates to the identification and characterization of a new class of compounds which present an anti-cell proliferation effect, more particularly on tumor cells. Without being bound by any theory, this effect is believed to be due to an activity on cell signaling, as described above. In particular, as illustrated in the examples, the compounds of this invention inhibit the oncogenic properties of the above family of proteins, potentially by impairing the nucleotide exchange. Advantageously, these compounds will inhibit or reverse malignant cell phenotypes in a wide array of human tissues, have little or no effect on normal cell physiology, will be highly active so that a limited number of treatments will be needed for each patient, and will have excellent bio availability and pharmacokinetic properties.

Accordingly, one aspect of the invention is to provide a compound having a general formula (I):

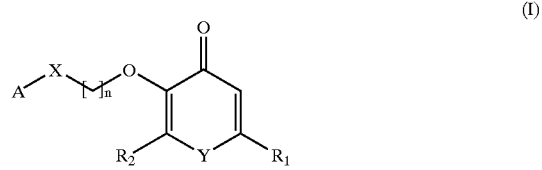

wherein:

$R_1$ is $CH_2R_3$ or $COR_3$;

$R_2$ represents a hydrogen atom or an alkenyl group containing from 3 to 6 carbon atoms;

$R_3$ is —OH, —$OR_4$, —$SR_4$, —$NR_5R_6$, or

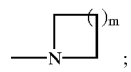

$R_4$ represents a group selected from alkyl containing from 1 to 6 carbon atoms, aryl, aralkyl, alkanoyl from 2 to 6 carbon atoms and arylcarbonyl;

$R_5$ and $R_6$, independently from each other, are selected from a hydrogen atom, an alkyl group having from 1 to 10 carbon atoms, an aryl and an aralkyl;

m is 2 or 3;

n represents an integer between 1 and 10 inclusive;

X represents an oxygen atom, a sulfur atom or a radical —$NR_7$—;

Y represents an oxygen atom, a sulfur atom or a radical —$NR_7$—;

$R_7$, identical or different, is selected in a group consisting of a hydrogen atom, an alkyl group having from 1 to 10 carbon atoms, an aryl and an aralkyl;

A represents either a substituted phenyl group of formula

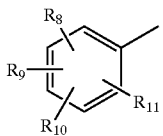

in which:

$R_8$, $R_9$, $R_{10}$ and $R_{11}$, independently from each other, are selected from a hydrogen atom, a halogen atom (preferably F, Cl, or Br), a hydroxyl group, a ($C_1$–$C_{10}$)alkyl group, an ($C_1$–$C_{10}$)alkanoyl group, a ($C_1$–$C_{10}$)alkoxy group, an aryl group, an aralkyl group, an arylcarbonyl group, a mono- or poly-cyclic hydrocarbon group, —$NO_2$, —CN, a —$NR_{12}R_{13}$ group or a trifluoro($C_1$–$C_6$)alkyl group; $R_8$, $R_9$, $R_{10}$ and $R_{11}$, not being simultaneously hydrogen atom, or alternatively two substituents, $R_8$ and $R_9$, may form together a mono- or poly-cyclic hydrocarbon group with the carbon atoms of the phenyl group they are attached and the two other substituents, $R_{10}$ and $R_{11}$, are as defined above;

or A represents a 5- or 6-membered heterocyclic ring which has 1 to 3 hetero-atoms selected from oxygen, sulfur and nitrogen, said ring is bonded directly to X;

$R_{12}$ and $R_{13}$, independently from each other, are selected in the group consisting of a hydrogen atom, an alkyl group having from 1 to 10 carbon atoms, an aryl and an aralkyl;

with the provisos that:

when X and Y are oxygen atoms, $R_2$ is a hydrogen atom, n is 5 and $R_8$ on the ortho position on the phenyl group vis-à-vis X is n-propyl group, then $R_9$, $R_{10}$ and $R_{11}$ are different from hydrogen;

when X and Y are oxygen atoms, $R_2$ is a hydrogen atom, n is 5, $R_8$ on the ortho position on the phenyl group vis-à-vis X is n-propyl group, $R_9$ on the meta position vis-à-vis X is an hydroxyl group, and $R_{10}$ on the para position vis-à-vis X is an acetyl group; then $R_{11}$ is different from hydrogen;

when X and Y are oxygen atoms, $R_2$ is a hydrogen atom, n is 2 or 3, then A is different from a non-substituted naphthalene group;

its tautomers, optical and geometrical isomers, racemates, salts, hydrates and mixtures thereof.

The compounds of the present invention may have one or more asymmetric centers and it is intended that stereoisomers (optical isomers), as separated, pure or partially purified stereoiomers or racemic mixtures thereof are included in the scope of the invention.

The present invention also relates to pharmaceutical compositions comprising at least one compound as defined above in a pharmaceutically acceptable support, optionally in association with another active agent.

The present invention also relates to the use of a compound as defined above, for the manufacture of a medicament for the treatment of diseases associated with abnormal cell proliferation, such as cancers.

The present invention also includes methods of treating diseases associated with abnormal cell proliferation, such as cancers, comprising the administration to a subject in need thereof of an effective amount of a compound as defined above.

As will be further disclosed in this application, the compounds according to this invention have strong cell proliferation inhibitory activity and are effective at reducing or arresting growth of proliferating cells such as tumor cells.

PREFERRED EMBODIMENTS

Within the context of the present application, the terms alkyl and alkoxy denote linear or branched saturated groups containing from 1 to 6 carbon atoms. An alkoxy group denotes an —O-alkyl group.

The alkyl groups may be linear or branched. Examples of alkyl groups having from 1 to 10 carbon atoms inclusive are methyl, ethyl, propyl, isopropyl, t-butyl, n-butyl, pentyl, hexyl, heptyl, octyl, nonyl, decyl, 2-ethylhexyl, 2-methylbutyl, 2-methylpentyl, 1-methylhexyl, 3-methylheptyl and the other isomeric forms thereof. Preferably, the alkyl groups have from 1 to 6 carbon atoms.

The alkenyl groups may be linear or branched. Examples of alkenyl containing from 3 to 6 carbon atoms are 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the isomeric forms thereof.

The term aryl includes any aromatic group comprising preferably from 5 to 14 carbon atoms, preferably from 6 to 14 carbon atoms, optionally interrupted by one or several heteroatoms selected from N, O, S or P. Most preferred aryl groups are mono- or bi-cyclic and comprises from 6 to 14 carbon atoms, such as phenyl, α-naphtyl, β-naphtyl, antracenyl, or fluorenyl group.

The term aralkyl group generally stands for an aryl group attached to an alkyl group as defined above, such as benzyl or phenethyl.

The term mono- or poly-cyclic hydrocarbon group is understood to refer to hydrocarbon cyclic group having from 1 to 20 carbon atoms, optionally interrupted with one or more heteroatoms selected in the group N, O, S and P. Among such mono- or poly-cyclic hydrocarbon groups, cyclopentyl, cyclohexyl, cycloheptyl, 1- or 2-adamantyl groups, pyran, piperidine, pyrrolidine, morpholine, dioxan, tetrahydrothiophene, and tetrahydrofuran can be cited. The mono- or poly-cyclic hydrocarbon group may form with the phenyl group it is attached an aryl group, such as a α-naphtyl, β-naphtyl, or antracenyl group.

An alkanoyl group is a —CO-alkyl group, the alkyl group being as defined above.

The term arylcarbonyl group generally stands for an aryl group attached to a carbonyl group, the aryl group being as defined above.

The term 5- or 6-membered heterocyclic ring includes pyrrole, pyridine, furan, thiophene, pyrimidine, pyrazine, imidazole, thiazole, oxazole, indole, purine, benzo[b]furan, benzo[b]thiophene, isoquinoline, quinoline, 6,7-dihydro-5H-(2)pyridine, 1H-pyrazolo[3,4-b]pyridine, thienopyridine.

The alkyl, alkenyl, aryl, aralkyl, mono- or poly-cyclic hydrocarbon group, and the 5- or 6-membered heterocyclic ring may be optionally substituted with one or more groups selected from hydroxyl group, halogen atom, cyano group, nitro group, ester (—COO($C_1$–$C_6$)alkyl group), —OCO ($C_1$–$C_6$)alkyl group, amide (—NHCO($C_1$–$C_6$)alkyl or —CONH($C_1$–$C_6$)alkyl group), ($C_1$–$C_{10}$)alkyl radical, ($C_1$–$C_{10}$)alkoxy radical, mono- or poly-cyclic hydrocarbon group, C=O group, a —$NR_{12}R_{13}$ group or a trifluoro ($C_1$–$C_6$)alkyl group.

Preferably, $R_{12}$ and $R_{13}$ are hydrogen atom or ethyl group.

The trifluoro($C_1$–$C_6$)alkyl group is preferably the trifluoromethyl group.

In a particular embodiment, when $R_3$ represents —$NR_5R_6$, preferably $R_5$ is a hydrogen atom and $R_6$ is selected from an alkyl group having from 1 to 10 carbon atoms, an aryl and an aralkyl.

According to preferred embodiments, the compounds according to the invention correspond to general formula (I) wherein:

X is oxygen; and/or

Y is oxygen; and/or n is from 4 to 7 inclusive; and/or $R_1$ is —$CH_2OH$, —$CH_2$—O-benzyl, —$CO_2H$ or —CO—NH-benzyl; and/or $R_2$ is a hydrogen atom or a propen-1-yl group; and/or A is a substituted phenyl as defined above.

In a preferred embodiment, when A is a substituted phenyl, the substituted phenyl presents the following formula:

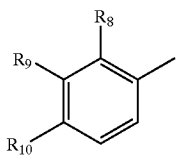

In a particular embodiment, when A is a substituted phenyl as defined above, at least one of the substituents on the phenyl group is an halogen atom, more preferably chlorine.

A particular preferred group of compounds according to the present invention, are the compounds of formula (I) wherein at least two substituents simultaneously represent Cl.

Another particular preferred group of compounds according to the present invention, are the compounds of formula (I) wherein $R_8$ represents a hydrogen atom, a propyl group or an ethoxy group, $R_9$ and $R_{10}$ represent a hydrogen atom, or an halogen atom, preferably chlorine, and $R_{11}$ is a hydrogen atom.

When the compounds according to the invention are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents may also be used.

Specific examples of compounds of formula (I) which fall within the scope of the present invention include the following compounds:

5-[5-(4-Chlorophenyloxy)pentyloxy]-2-(hydroxymethyl)-4H-pyran-4-one

5-[5-(3-Chlorophenyloxy)pentyloxy]-2-(hydroxymethyl)-4H-pyran-4-one

5-[5-(3,4-Dichlorophenyloxy)pentyloxy]-2-(hydroxymethyl)-4H-pyran-4-one

5-[4-(3,4-Dichlorophenyloxy)butyloxy]-2-(hydroxymethyl)-4H-pyran-4-one

5-[5-(3,4-Dichloro-2-propylphenyloxy)pentyloxy]-2-(hydroxymethyl)-4H-pyran-4-one 5-[5-(4,5-Dichloro-2-propylphenyloxy)pentyloxy]-2-(hydroxymethyl)-4H-pyran-4-one 5-[5-(2-Ethyloxyphenyloxy)pentyloxy]-2-(hydroxymethyl)-4H-pyran-4-one 5-[6-(3,4-Dichloro-2-propylphenyloxy)hexyloxy]-2-(hydroxymethyl)-4H-pyran-4-one 5-[7-(3,4-Dichloro-2-propylphenyloxy)heptyloxy]-2-(hydroxymethyl)-4H-pyran-4-one 5-[9-(3,4-Dichlorophenyloxy)nonyloxy]-2-(hydroxymethyl)-4H-pyran-4-one 2-(Benzyloxymethyl)-5-[5-(3,4-dichlorophenyloxy)pentyloxy]-2-(hydroxymethyl)-4H-pyran-4-one 5-[5-(4-Chlorophenyloxy)pentyloxy]-4-oxo-4H-pyran-2-carboxylic acid 5-[5-(3-Chlorophenyloxy)pentyloxy]-4-oxo-4H-pyran-2-carboxylic acid 5-[5-(3,4-Dichlorophenyloxy)pentyloxy]-4-oxo-4H-pyran-2-carboxylic acid 5-[4-(3,4-Dichlorophenyloxy)butyloxy]-4-oxo-4H-pyran-2-carboxylic acid 5-[5-(3,4-Dichloro-2-propylphenyloxy)pentyloxy]-4-oxo-4H-pyran-2-carboxylic acid 5-[5-(2-Ethyloxyphenyloxy)pentyloxy]-4-oxo-4H-pyran-2-carboxylic acid N-Benzyl-5-[5-(4-chlorophenyloxy)pentyloxy]-4-oxo-4H-pyran-2-carboxamide (E)-3-[5-(4-Chlorophenyloxy)pentyloxy]-6-(hydroxymethyl)-2-(propen-1-yl)-4H-pyran-4-one
(E)-3-[5-(3-Chlorophenyloxy)pentyloxy]-6-(hydroxymethyl)-2-(propen-1-yl)-4H-pyran-4-one
(E)-3-[5-(3,4-Chlorophenyloxy)pentyloxy]-6-(hydroxymethyl)-2-(propen-1-yl)-4H-pyran-4-one
(E)-3-[5-(3,4-Chloro-2-propylphenyloxy)pentyloxy]-6-(hydroxymethyl)-2-(propen-1-yl)-4H-pyran-4-one
(E)-6-(Hydroxymethyl)-2-(propen-1-yl)-3-[5-(2-propylphenyloxy)pentyloxy]-4H-pyran-4-one
(E)-3-[5-(4-Chlorophenyloxy)pentyloxy]-2-(propen-1-yl)-4-oxo-4H-pyran-6-carboxylic acid
(E)-3-[5-(3-Chlorophenyloxy)pentyloxy]-2-(propen-1-yl)-4-oxo-4H-pyran-6-carboxylic acid
(E)-3-[5-(3,4-Dichlorophenyloxy)pentyloxy]-2-(propen-1-yl)-4-oxo-4H-pyran-6-carboxylic acid
(E)-3-[5-(3,4-Dichloro-2-propylphenyloxy)pentyloxy]-2-(propen-1-yl)-4-oxo-4H-pyran-6-carboxylic acid
(E)-2-(Propen-1-yl)-3-[5-(2-propylphenyloxy)pentyloxy]-4-oxo-4H-pyran-6-carboxylic acid.

A particularly preferred compound is 5-[5-(3,4-dichloro-2-propylphenyloxy)pentyloxy]-2-(hydroxymethyl)-4H-pyran-4-one.

The compounds according to the present invention may be prepared by various methods known to those skilled in the art. More preferably, two chemical routes have been carried out. The first one (Scheme 1) includes an alkylation of kojic acid with the corresponding alkylbromide, which gives rise to the desired 2-(hydroxymethyl)-4H-pyran-4-ones 1. These compounds may be then oxidized, typically with chromium trioxide in sulfuric acid, to produce the acid derivatives 2, which can be readily converted into the corresponding analogues of general structure 3. Additionally, the hydroxymethyl derivatives 1 provide the compounds 4 by standard procedures.

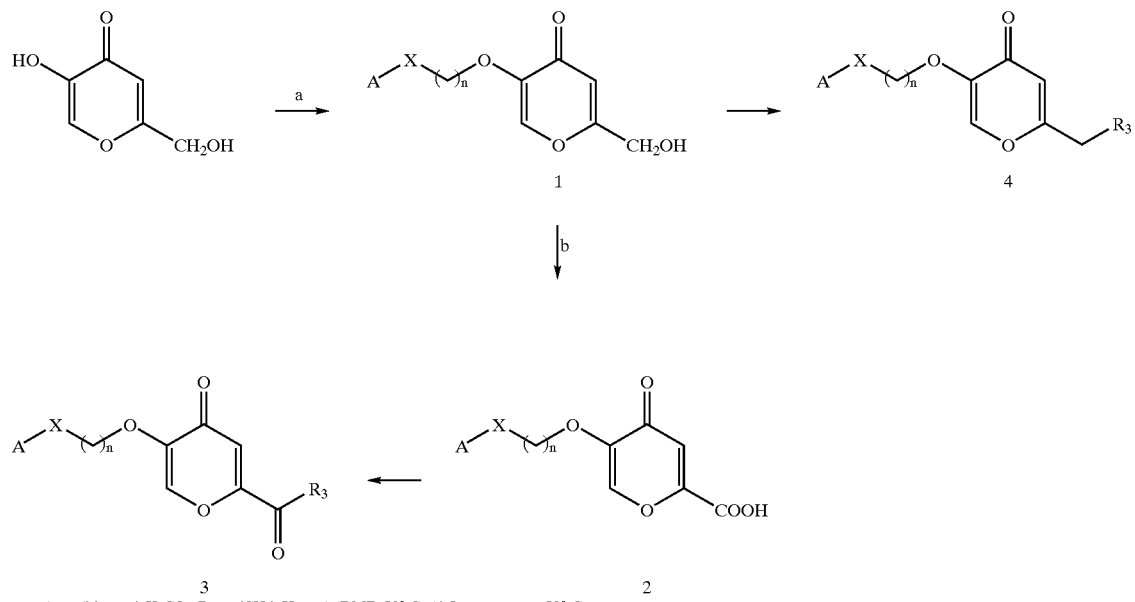

Scheme 1

Reagents and conditions: a) K$_2$CO$_3$, Br—(CH$_2$)$_n$X—A, DMF, 50° C.; b) Jones reagent, 50° C. to rt, acetone;

Step a) of this method is more preferably conducted in a solvent, such as DMF, at a temperature comprised between 40 and 70° C., typically around 50° C.

In step b), the compounds are preferably reacted in the presence of the Jones reagent and in a solvent, such as acetone, while the temperature is decreased to reach room temperature.

The second preferred chemical route (Scheme 2) corresponds to an alkylation of kojic acid with allylbromide, which gives rise the 4H-pyran-4-one derivative 5. This compound is then thermally isomerised to 6. The general protocol for the O-alkylation produces simultaneously not only the alkylation but also the migration of the double bond to the conjugated position affording derivatives 7. These alcohols are oxidized with Jones reagent to provide the acids of general structure 8. Compounds 7 and 8 are derived to give analogues 9 and 10.

Scheme 2

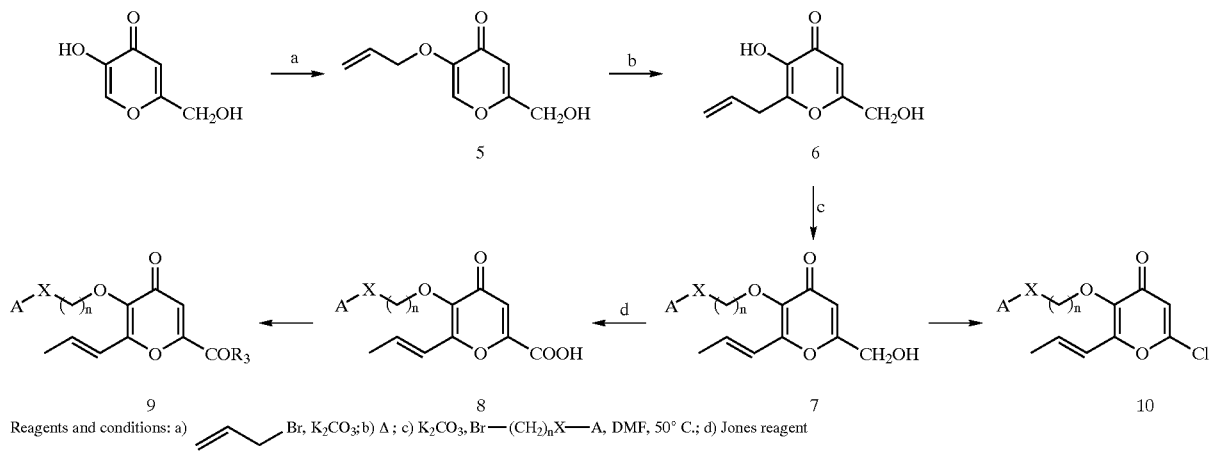

Reagents and conditions: a) 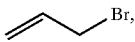 Br, K₂CO₃; b) Δ ; c) K₂CO₃, Br—(CH₂)ₙX—A, DMF, 50° C.; d) Jones reagent For both described series, yields are generally comprised between 55 and 75% by weight. These methods for preparing compounds of formula (I) represent further objects of the present application.

It should be understood that other ways of producing these compounds may be designed by the skilled person, based on common general knowledge and following guidance contained in this application.

In order to prepare compounds of formula (I) wherein Y is $NR_7$, kojic acid can be first protected on the hydroxyl group and then be reacted with $R_7NH_2$ to give rise a N-pyridone derivative (J. Heterocyclic Chemistry, 1986, 23 : 5–8). This N-pyridone derivative is thereafter deprotected and may react as described above following schemes 1 and 2. Another synthesis of N-substituted-pyridone is described by Korenova, A et al. in J. Chem. Pap, 1997, No.6, 51, 383–389.

As indicated above, a further object of this invention relates to a pharmaceutical composition comprising at least one compound of formula (I), as defined above, and a pharmaceutically acceptable vehicle or support.

The compounds may be formulated in various forms, including solid and liquid forms, such as tablets, gel, syrup, powder, aerosol, etc.

The compositions of this invention may contain physiologically acceptable diluents, fillers, lubricants, excipients, solvents, binders, stabilizers, and the like. Diluents that may be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that may be used in the compositions include but are not limited to starch, gelatin and fillers such as sucrose, glucose, dextrose and lactose.

Natural and synthetic gums that may be used in the compositions include but are not limited to sodium alginate, ghatti gum, carboxymethyl cellulose, methyl cellulose, polyvinyl pyrrolidone and veegum. Excipients that may be used in the compositions include but are not limited to microcrystalline cellulose, calcium sulfate, dicalcium phosphate, starch, magnesium stearate, lactose, and sucrose. Stabilizers that may be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that may be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds of formula (I) are administered will vary according to the dosage form, mode of administration, the condition being treated and particulars of the patient being treated. Accordingly, optimal therapeutic concentrations will be best determined at the time and place through routine experimentation.

The compounds according to the invention can also be used enterally. Orally, the compounds according to the invention are suitable administered at the rate of 100 µg to 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance.

The compounds according to the invention can also be administered parenterally in the form of solutions or suspensions for intravenous or intramuscular perfusions or injections. In that case, the compounds according to the invention are generally administered at the rate of about 10 µg to 10 mg per day per kg of body weight; a preferred method of administration consists of using solutions or suspensions containing approximately from 0.01 mg to 1 mg of active substance per ml.

The compounds of formula (I) can be used in a substantially similar manner to other known anti-tumor agents for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on compounds found to have anti-tumor properties.

According to another aspect, the present invention relates to a method for the treatment of a disease associated with abnormal cell proliferation, comprising administering to a patient in need of such treatment an effective amount of at least one compound of general formula (I) as described above, wherein, in said formula (I):

$R_1$ is $CH_2R_3$ or $COR_3$;

$R_2$ represents a hydrogen atom or an alkenyl group containing from 3 to 6 carbon atoms;

$R_3$ is —OH, —$OR_4$, —$SR_4$, —$NR_5R_6$, or

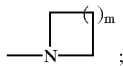

$R_4$ represents a group selected from alkyl containing from 1 to 6 carbon atoms, aryl, aralkyl, alkanoyl from 2 to 6 carbon atoms and arylcarbonyl;

$R_5$ and $R_6$, independently from each other, are selected from a hydrogen atom, an alkyl group having from 1 to 10 carbon atoms, an aryl and an aralkyl;

m is 2 or 3;

n represents an integer between 1 and 10 inclusive;

X represents an oxygen atom, a sulfur atom or a radical —$NR_7$—;

Y represents an oxygen atom, a sulfur atom or a radical —$NR_7$—;

$R_7$, identical or different, is selected in a group consisting of a hydrogen atom, an alkyl group having from 1 to 10 carbon atoms, an aryl and an aralkyl;

A represents either a substituted phenyl group of formula

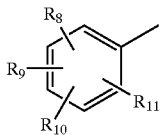

in which:

$R_8$, $R_9$, $R_{10}$ and $R_{11}$, independently from each other, are selected from a hydrogen atom, a halogen atom (preferably F, Cl, or Br), a hydroxyl group, a ($C_1$–$C_{10}$)alkyl group, an ($C_1$–$C_{10}$)alkanoyl group, a ($C_1$–$C_{10}$)alkoxy group, an aryl group, an aralkyl group, an arylcarbonyl group, a mono- or poly-cyclic hydrocarbon group, —$NO_2$, —CN, a —$NR_{12}R_{13}$ group or a trifluoro($C_1$–$C_6$)alkyl group; $R_8$, $R_9$, $R_{10}$ and $R_{11}$ not being simultaneously hydrogen atom, or alternatively two substituents, $R_8$ and $R_9$, may form together a mono- or poly-cyclic hydrocarbon group with the carbon atoms of the phenyl group they are attached and the two other substituents, $R_{10}$ and $R_{11}$, are as defined above;

or A represents a 5- or 6-membered heterocyclic ring which has 1 to 3 hetero-atoms selected from oxygen, sulfur and nitrogen, said ring is bonded directly to X;

$R_{12}$ and $R_{13}$, independently from each other, are selected in the group consisting of a hydrogen atom, an alkyl group having from 1 to 10 carbon atoms, an aryl and an aralkyl;

its tautomers, optical and geometrical isomers, racemates, salts, hydrates and mixtures thereof.

Preferred compounds for use according to the invention include any sub-group as defined above, and, as specific examples, the following compounds:

5-[5-(4-Chlorophenyloxy)pentyloxy]-2-(hydroxymethyl)-4H-pyran-4-one

5-[5-(3-Chlorophenyloxy)pentyloxy]-2-(hydroxymethyl)-4H-pyran-4-one

5-[5-(3,4-Dichlorophenyloxy)pentyloxy]-2-(hydroxymethyl)-4H-pyran-4-one

5-[4-(3,4-Dichlorophenyloxy)butyloxy]-2-(hydroxymethyl)-4H-pyran-4-one

5-[5-(3,4-Dichloro-2-propylphenyloxy)pentyloxy]-2-(hydroxymethyl)-4H-pyran-4-one 5-[5-(4,5-Dichloro-2-propylphenyloxy)pentyloxy]-2-(hydroxymethyl)-4H-pyran-4-one 5-[5-(2-Ethyloxyphenyloxy)pentyloxy]-2-(hydroxymethyl)-4H-pyran-4-one 5-[6-(3,4-Dichloro-2-propylphenyloxy)hexyloxy]-2-(hydroxymethyl)-4H-pyran-4-one 5-[7-(3,4-Dichloro-2-propylphenyloxy)heptyloxy]-2-(hydroxymethyl)-4H-pyran-4-one 5-[9-(3,4-Dichlorophenyloxy)nonyloxy]-2-(hydroxymethyl)-4H-pyran-4-one 2-(Benzyloxymethyl)-5-[5-(3,4-dichlorophenyloxy)pentyloxy]-2-(hydroxymethyl)-4H-pyran-4-one 5-[5-(4-Chlorophenyloxy)pentyloxy]-4-oxo-4H-pyran-2-carboxylic acid 5-[5-(3-Chlorophenyloxy)pentyloxy]-4-oxo-4H-pyran-2-carboxylic acid 5-[5-(3,4-Dichlorophenyloxy)pentyloxy]-4-oxo-4H-pyran-2-carboxylic acid 5-[4-(3,4-Dichlorophenyloxy)butyloxy]-4-oxo-4H-pyran-2-carboxylic acid 5-[5-(3,4-Dichloro-2-propylphenyloxy)pentyloxy]-4-oxo-4H-pyran-2-carboxylic acid 5-[5-(2-Ethyloxyphenyloxy)pentyloxy]-4-oxo-4H-pyran-2-carboxylic acid N-Benzyl-5-[5-(4-chlorophenyloxy)pentyloxy]-4-oxo-4H-pyran-2-carboxamide (E)-3-[5-(4-Chlorophenyloxy)pentyloxy]-6-(hydroxymethyl)-2-(propen-1-yl)-4H-pyran-4-one (E)-3-[5-(3-Chlorophenyloxy)pentyloxy]-6-(hydroxymethyl)-2-(propen-1-yl)-4H-pyran-4-one (E)-3-[5-(3,4-Chlorophenyloxy)pentyloxy]-6-(hydroxymethyl)-2-(propen-1-yl)-4H-pyran-4-one (E)-3-[5-(3,4-Chloro-2-propylphenyloxy)pentyloxy]-6-(hydroxymethyl)-2-(propen-1-yl)-4H-pyran-4-one (E)-6-(Hydroxymethyl)-2-(propen-1-yl)-3-[5-(2-propylphenyloxy)pentyloxy]-4H-pyran-4-one (E)-3-[5-(4-Chlorophenyloxy)pentyloxy]-2-(propen-1-yl)-4-oxo-H-pyran-6-carboxylic acid (E)-3-[5-(3-Chlorophenyloxy)pentyloxy]-2-(propen-1-yl)-4-oxo-4H-pyran-6-carboxylic acid (E)-3-[5-(3,4-Dichlorophenyloxy)pentyloxy]-2-(propen-1-yl)-4-oxo-4H-pyran-6-carboxylic acid (E)-3-[5-(3,4-Dichloro-2-propylphenyloxy)pentyloxy]-2-(propen-1-yl)-4-oxo-4H-pyran-6-carboxylic acid (E)-2-(Propen-1-yl)-3-[5-(2-propylphenyloxy)pentyloxy]-4-oxo-4H-pyran-6-carboxylic acid A further object of this invention is the use of an effective amount of at least one compound of formula (I) as defined above for the preparation of pharmaceutical composition for the treatment of a disease associated with abnormal cell proliferation.

Because of their cell proliferation inhibitory activity, the compounds of this invention are suitable for treating a variety of diseases in a variety of conditions. In this regard, "treatment" or "treating" include both therapeutic and prophylactic treatments. Accordingly, the compounds may be used at very early stages of a disease, or before early onset, or after significant progression, including metastasis. The term "treatment" or "treating" designates in particular a reduction of the burden in a patient, such as a reduction in cell proliferation rate, a destruction of diseased proliferative cells, a reduction of tumor mass or tumor size, a delaying of tumor progression, as well as a complete tumor suppression.

Typical examples of diseases associated with abnormal cell proliferation include cancers and restenosis, for instance. The compounds of this invention are particularly suited for the treatment of cancers, such as solid tumors or lymphoid tumors. Specific examples include prostate cancer, ovarian cancer, pancreas cancer, lung cancer, breast cancer, liver cancer, head and neck cancer, colon cancer, bladder cancer, non-Hodgkin's lymphoma cancer and melanoma.

The compounds may be administered according to various routes, typically by injection, such as local or systemic injection(s). Intratumoral injections are preferred for treating existing cancers. However, other administration routes may be used as well, such as intramuscular, intravenous, intradermic, subcutaneous, etc. Furthermore, repeated injections may be performed, if needed, although it is believed that limited injections will be needed in view of the efficacy of the compounds.

A further object of this invention is a method for reducing cancer cell proliferation by administering in a subject having cancer an effective amount of compound of formula (I) as defined above.

A further object of this invention is a method for treating metastatic cancers by administering in a subject in need of such treatment an effective amount of compound of formula (I) as defined above.

A further object of this invention is the use of a compound as defined above for the preparation of a pharmaceutical composition for treating metastatic cancers or for reducing cancer cell proliferation.

Further aspects and advantages of this invention will be disclosed in the following examples, which should be regarded as illustrative and not limiting the scope of this application.

LEGEND TO THE FIGURES

FIG. 1: Number of neoR NIH3T3 colonies after transfection with a vector expressing an activated Ras (RasVal12) as compared to an empty vector, in the presence or not of compound EH22900.

Figure 2:
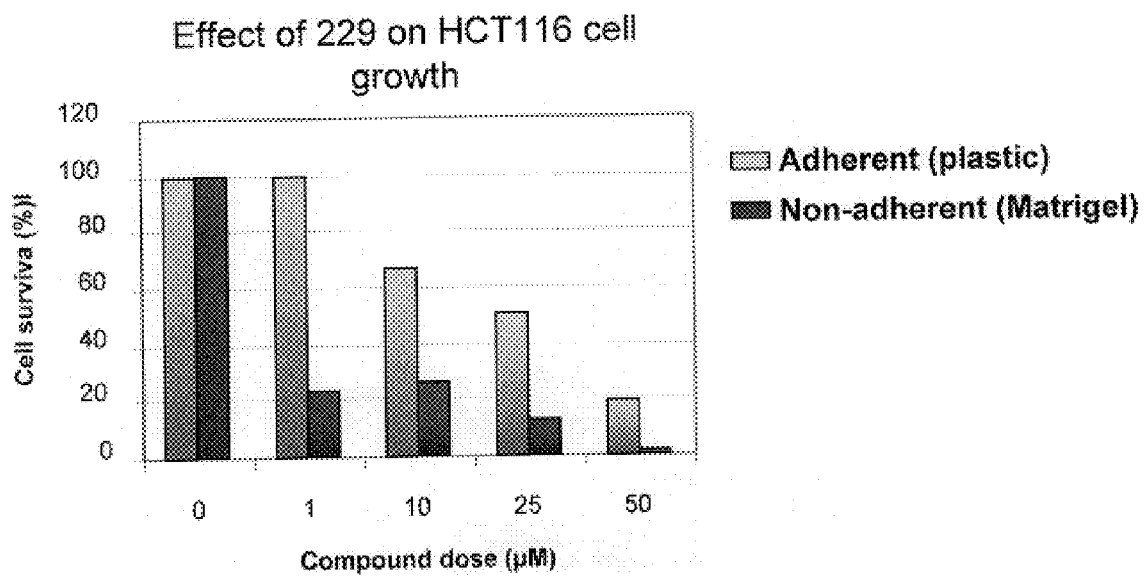

FIG. 2: Cell survival of HCT116 cells treated with compound EH22900 in adherent and non-adherent culture conditions.

Figure 3:
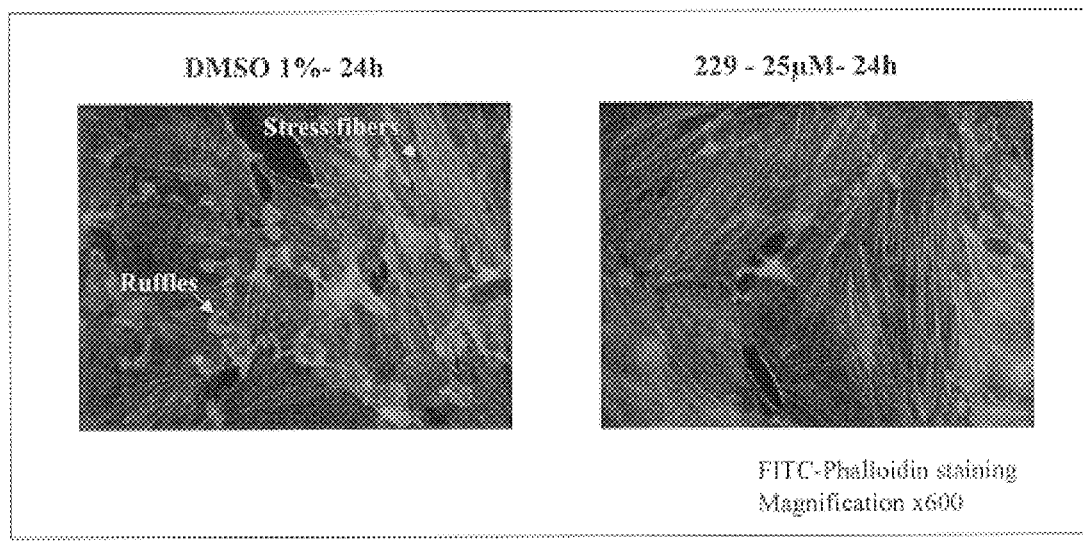

FIG. 3: Staining of NIH3T3 fibroblasts with FITC-coupled phalloidin which specifically binds to actin filaments, in the presence or not of compound EH22900.

Figure 4:
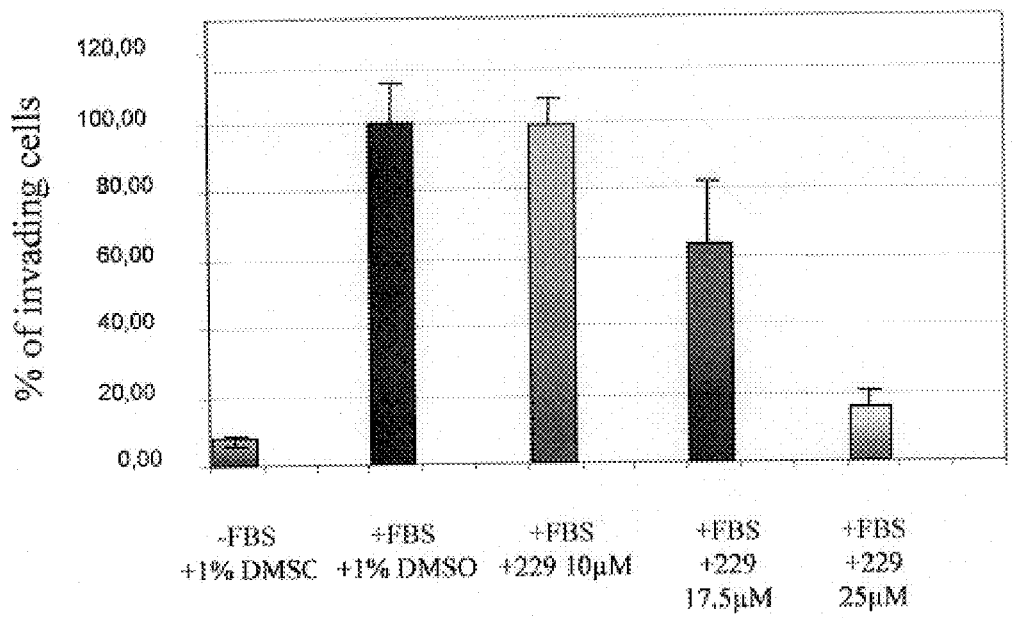

FIG. 4: Percentage of invading MDA-MB-231 cells treated with 1% DMSO or different concentrations of compound EH22900 as measured in a Boyden chamber.

Figure 5:
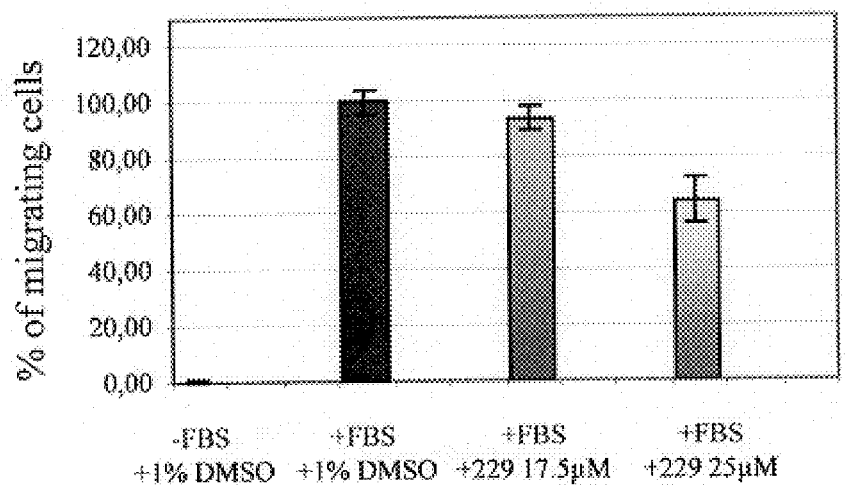

FIG. 5: Percentage of migrating MDA-MB-231 cells treated with 1% DMSO or different concentrations of compound EH22900 as measured in a Boyden chamber.

EXAMPLES

Examples 1 to 29 disclose the synthesis and physico-chemical properties of compounds according to this invention.

Example 30 discloses the biological activity of the compounds.

Example 1

5-[5-(4-Chlorophenyloxy)pentyloxy]-2-(hydroxymethyl)-4H-pyran-4-one (EH15500)

The compound was prepared according to Scheme 1. The structure of compound ex 1 is presented below:

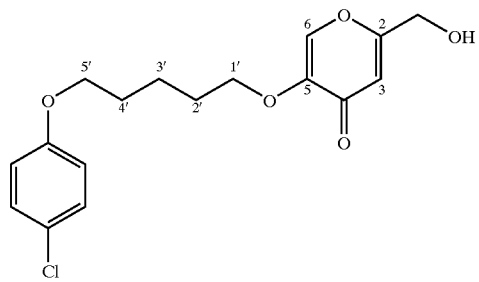

Yield: 75%; solid, mp: 95–97° C. (EtOAc/Hexane).

$R_f$: 0.2 (EtOAc).

IR (KBr, cm$^{-1}$): 3265, 3088, 2951, 1641, 1610, 1589, 1491, 1263, 1238, 1227.

$^1$H-NMR (CDCl$_3$, δ): 1.50–1.68 (m, 2H, 2H$_{3'}$), 1.72–1.85 (m, 4H, 2H$_{2'}$, 2H$_{4'}$), 3.35 (t, J=6.1 Hz, 1H, OH), 3.80 (t, J=6.4 Hz, 2H, 2H$_{1'}$ or 2H$_{5'}$), 3.87 (t, J=6.4 Hz, 2H, 2H$_{5'}$ or 2H$_{1'}$), 4.41 (d, J=6.1 Hz, 2H, CH$_2$OH), 6.44 (s, 1 H, H$_3$), 6.73 (d, J=9.0 Hz, 2H, H$_2$, H$_6$ Ar—H), 7.15 (d, J=9.0 Hz, 2H, H$_3$, H$_5$ Ar—H), 7.49 (s, 1H, H$_6$).

$^{13}$C-NMR (CDCl$_3$, δ): 22.3, 28.6, 28.7, 60.7, 67.8, 69.4, 111.8, 115.6, 127.1, 129.1, 139.2, 147.7, 157.4, 166.8, 174.6.

Elemental analysis for C$_{17}$H$_9$O$_5$Cl Calculated: C, 60.23%; H, 5.61%. Found: C, 60.28%; H, 5.91%.

Example 2

5-[5-(3-Chlorophenyloxy)pentyloxy]-2-(hydroxymethyl)-4H-pyran-4-one (EH10600)

The compound was prepared according to Scheme 1. The structure of compound ex 2 is presented below:

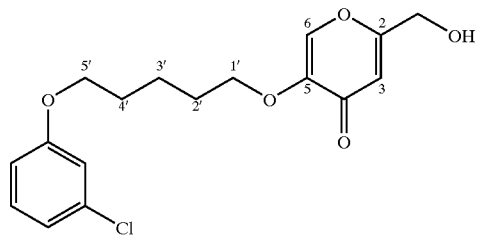

Yield: 71%; solid, mp: 87–88° C. (EtOAc/Hexane).

$R_f$: 0.2 (EtOAc).

IR (KBr, cm$^{-1}$): 3248, 3082, 3060, 2955, 2906, 2874, 1645, 1608, 1589, 1573, 1479, 1452, 1278.

$^1$H-NMR (CDCl$_3$, δ): 1.45–1.61 (m, 2H, 2H$_3$·), 1.69–1.87 (m, 4H, 2H$_2$·, 2H$_4$·), 3.79 (t, J=6.3 Hz, 2H, 2H$_1$· or 2H$_5$·), 3.87 (t, J=6.3 Hz, 2H, 2H$_5$· or 2H$_1$·), 3.99 (t, J=6.4 Hz, 1H, OH), 4.41 (d, J=6.4 Hz, 2H, CH$_2$OH), 6.45 (s, 1H, H$_3$), 6.71 (dd, J=2.4, 0.8 Hz, 1H, H$_2$ Ar—H), 6.83 (m, 2H, H$_4$, H$_6$ Ar—H), 7.11 (t, J=8.1 Hz, 1H, H$_5$ Ar—H), 7.55 (s, 1H, H$_6$).

$^{13}$C-NMR (CDCl$_3$, δ): 22.6, 28.8, 28.9, 60.9, 67.9, 69.6, 111.9, 113.1, 115.1, 120.8, 130.3, 134.9, 139.5, 147.9, 159.8, 167.6, 175.1.

Elemental analysis for C$_{17}$H$_{19}$O$_5$Cl Calculated: C, 60.23%; H, 5.61%. Found: C, 60.20%; H, 5.59%.

Example 3

5-[5-(3,4-Dichlorophenyloxy)pentyloxy]-2-(hydroxymethyl)-4H-pyran-4-one (EH5500)

The compound was prepared according to Scheme 1. The structure of compound ex 3 is presented below:

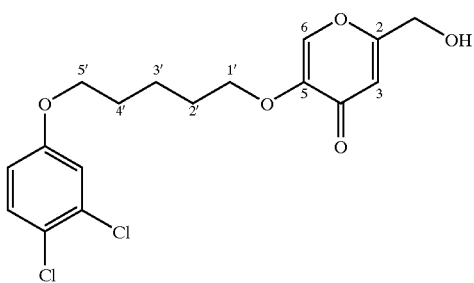

Yield: 73%; solid, mp: 97–99° C. (EtOAc/Hexane).

$R_f$: 0.2 (EtOAc).

IR (KBr, cm$^{-1}$): 3377, 3115, 3055, 2952, 2873, 1645, 1606, 1469, 1375, 1230, 1122, 1053, 918, 856.

$^1$H-NMR (CDCl$_3$, δ): 1.51–1.65 (m, 2H, 2H$_3$·), 1.76–1.86 (m, 4H, 2H$_2$·, 2H$_4$·), 3.40 (t, J=6.6 Hz, 1H, OH), 3.82 (t, J=6.3 Hz, 2H, 2H$_1$· or 2H$_5$·), 3.89 (t, J=6.3 Hz, 2H, 2H$_5$· or 2H$_1$·), 4.44 (d, J=6.4 Hz, 2H, CH$_2$OH), 6.49 (s, 1 H, H$_3$), 6.70 (dd, J=8.7, 3.5 Hz, 1H, H$_6$ Ar—H), 6.93 (d, J=3.5 Hz, 1H, H$_2$ Ar—H), 7.26 (d, J=8.7 Hz,1H, H$_5$ Ar—H), 7.53 (s,1H, H$_6$).

$^{13}$C-NMR (CDCl$_3$, δ): 22.4, 28.7, 60.6, 68.2, 69.4, 111.6, 114.4, 116.2, 123.6, 130.5, 132.7, 139.1, 147.7, 157.9, 167.7, 174.9.

Elemental analysis for C$_{17}$H$_{18}$O$_5$Cl$_2$ Calculated: C, 54.71%; H, 4.86%. Found: C, 54.66%; H, 5.02%.

Example 4

5-[4-(3,4-Dichlorophenyloxy)butyloxy]-2-(hydroxymethyl)-4H-pyran-4-one (EH17700)

The compound was prepared according to Scheme 1. The structure of compound ex 4 is presented below:

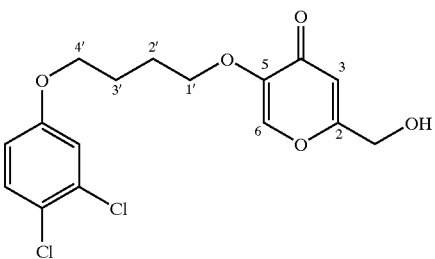

Yield: 73%; solid, mp: 107–108° C. (EtOAc/Hexane).

$R_f$: 0.2 (EtOAc).

IR (KBr, cm$^{-1}$): 3354, 3068, 2958, 2937, 2912, 1651, 1610, 1589, 1562, 1535, 1469, 1448, 1257, 827.

$^1$H-NMR (CDCl$_3$, δ): 1.74–1.83 (m, 4H, 2H$_2$·, 2H$_3$·), 3.71–3.81 (m, 5H, 2H$_1$·, 2H$_4$·, OH), 4.28 (d, J=5.7 Hz, 2H, CH$_2$OH), 6.32 (s, 1H, H$_3$), 6.53 (dd, J=8.5; 3.5 Hz, 1H, H$_6$ Ar—H), 6.77 (d, J=3.5 Hz, 1H, H$_2$ Ar—H), 7.07 (d, J=8.5 Hz, 1H, H$_5$ Ar—H), 7.37 (s, 1H, H$_6$).

$^{13}$C-NMR (CDCl$_3$, δ): 25.7, 25.8, 60.9, 68.1, 69.4, 111.9, 114.6, 116.1, 123.9, 130.8, 132.8, 139.7, 147.8, 158.1, 167.7, 175.1.

Elemental analysis for C$_{16}$H$_{16}$O$_5$Cl$_2$ Calculated: C, 53.48%; H, 4.46%. Found: C, 53.40%; H, 4.68%.

Example 5

5-[5-(3,4-Dichloro-2-propylphenyloxy)pentyloxy]-2-(hydroxymethyl)-4H-pyran-4-one (EH22900)

The compound was prepared according to Scheme 1. The structure of compound ex 5 is presented below:

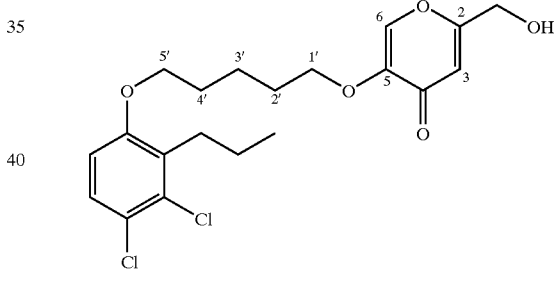

Yield: 73%; solid, mp: 85–86° C. (EtOAc/Et$_2$O).

$R_f$: 0.2 (EtOAc).

IR (KBr, cm$^{-1}$): 3300, 2945, 2870, 1647, 1607, 1452, 1259, 1207, 1151, 1082, 1026, 870.

$^1$H-NMR (CDCl$_3$, δ): 0.90 (t, J=8.3 Hz, 3H, CH$_3$), 1.39–1.62 (m, 4H, 2CH$_2$), 1.74–1.92 (m, 4H, 2CH$_2$), 2.73 (dd, J=7.9; 5.9 Hz, 2H, CH$_2$), 3.13 (br s, 1H, OH), 3.81–3.93 (m, 4H, 2CH$_2$O), 4.45 (s, 2H, CH$_2$OH), 6.52 (s, 1H, H$_3$), 6.63 (d, J=8.9 Hz, 1H—Ar), 7.17 (d, J=8.8 Hz, 1H, Ar—H), 7.72 (s, 1H, H$_6$).

$^{13}$C-NMR (CDCl$_3$, δ): 14.3, 21.9, 22.7, 28.9, 29.1, 30.2, 60.9, 68.3, 69.7, 110.4, 111.9, 127.5, 131.8, 139.6, 147.9, 156.2, 175.1.

Elemental analysis for C$_{20}$H$_{24}$O$_5$Cl$_2$ Calculated: C, 57.83%; H, 5.82%. Found: C, 57.96%; H, 5.72%.

Example 6

5-[5-(4,5-Dichloro-2-propylphenyloxy)pentyloxy]-2-(hydroxymethyl)-4H-pyran-4-one (EH30701)

The compound was prepared according to Scheme 1. The structure of compound ex 6 is presented below:

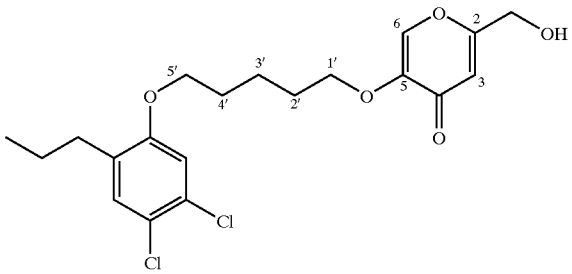

Yield: 60%; solid, mp: 83–84° C. (EtOAc/Et$_2$O).
R$_f$: 0.2 (EtOAc).
IR (KBr, cm$^{-1}$): 3315, 3082, 2952, 2927, 2873, 1649, 1608, 1587, 1450, 1263, 1215, 1151, 977.
$^1$H-NMR (CDCl$_3$, δ): 0.84 (t, J=7.3 Hz, 3H, CH$_3$), 1.39–1.62 (m, 4H, 2CH$_2$), 1.72–1.98 (m, 4H, 2CH$_2$), 2.47 (t, J=7.8 Hz, 2H, CH$_2$), 3.65 (br s, 1H, OH), 3.82–3.89 (m, 4H, 2CH$_2$O), 4.41 (s, 2H, CH$_2$OH), 6.45 (s, 1H, H$_3$), 6.78 (s, 1H, Ar—H), 7.08 (s, 1H, Ar—H), 7.50 (s, 1H, H$_6$).
$^{13}$C-NMR (CDCl$_3$, δ): 13.8, 22.4, 22.6, 28.6, 28.7, 31.5, 60.8, 68.1, 69.5, 111.9, 113.0, 122.9, 129.5, 130.7, 131.7, 139.4, 147.4, 155.8, 167.2, 174.8.
Elemental analysis for C$_{20}$H$_{24}$O$_5$Cl$_2$ Calculated: C, 57.83%; H, 5.82%. Found: C, 58.05%; H, 5.88%.

Example 7

5-[5-(2-Ethyloxyphenyloxy)pentyloxy]-2-(hydroxymethyl)-4H-pyran-4-one (EH18601)

The compound was prepared according to Scheme 1. The structure of compound ex 7 is presented below:

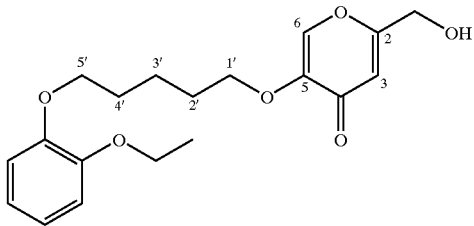

Yield: 75%; solid, mp: 75–76° C. (EtOAc-Et$_2$O).
R$_f$: 0.2 (EtOAc).
IR (CHCl$_3$, cm$^{-1}$): 3367, 3010, 2983, 2941, 2873, 1647, 1612, 1593, 1504, 1475, 1452, 1394, 1251, 1215, 1151, 1126, 866.
$^1$H-NMR (CDCl$_3$, δ): 1.35 (t, J=6.9 Hz, 3H, CH$_3$), 1.52–1.64 (m, 2H, CH$_2$), 1.74–1.91 (m, 4H, 2CH$_2$), 2.71 (br s, 1H, OH), 3.82 (t, J=6.5 Hz, 2H, CH$_2$O), 3.95 (t, J=6.5 Hz, 2H, CH$_2$O), 4.02 (q, J=7.1 Hz, 2H, CH$_2$O), 4.41 (s, 2H, CH$_2$OH), 6.47 (s, 1H, 1H$_3$), 6.82 (s, 4H, Ar—H), 7.51 (s, 1H, 1H$_6$).
$^{13}$C-NMR (CDCl$_3$, δ): 14.8, 22.3, 28.6, 28.7, 60.8, 64.5, 68.8, 69.5, 111.9, 113.9, 114.1, 121.0, 121.1, 139.3, 147.7, 148.8, 166.7, 174.6.
Elemental analysis for C$_{19}$H$_{24}$O$_6$ Calculated: C, 65.51%; H, 6.89%. Found: C, 65.41%; H, 7.03%.

Example 8

5-[6-(3,4-Dichloro-2-propylphenyloxy)hexyloxy]-2-(hydroxymethyl)-4H-pyran-4-one (EH16701)

The compound was prepared according to Scheme 1. The structure of compound ex 8 is presented below:

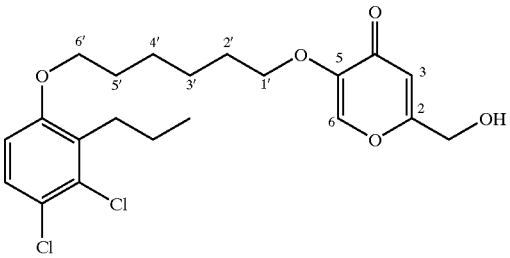

Yield: 75%; solid, mp: 86–87° C. (EtOAc/Et$_2$O).
R$_f$: 0.3 (EtOAc).
IR (KBr, cm$^{-1}$): 3301, 3099, 2937, 2908, 2756, 1645, 1610, 1591, 1456, 1253, 1080, 999.
$^1$H-NMR (CDCl$_3$, δ): 0.88 (t, J=7.4 Hz, 3H, CH$_3$), 1.37–1.56 (m, 6H, 3CH$_2$), 1.72–1.78 (m, 4H, 2CH$_2$), 2.71 (t, J=6.4 Hz, 2H, CH$_2$—Ar), 3.04 (br s, 1H, OH), 3.79 (t, J=6.9 Hz, 2H, CH$_2$O), 3.86 (t, J=6.2 Hz, 2H, CH$_2$O), 4.42 (s, 2H, CH$_2$OH), 6.47 (s, 1H, H$_3$), 6.61 (d, J=9.5 Hz, 1H, Ar—H), 7.15 (d, J=8.6 Hz, 1H, Ar—H), 7.51 (s, 1H, H$_6$).
$^{13}$C-NMR (CDCl$_3$, δ): 14.1, 21.8, 25.5, 25.8, 28.9, 29.1, 30.0, 60.9, 68.2, 69.6, 110.2, 111.9, 125.1, 126.3, 127.3, 132.5, 139.3, 147.8, 156.7, 167.5, 175.2.
Elemental analysis for C$_{21}$H$_{26}$Cl$_2$O$_5$ Calculated: C, 58.75%; H, 6.10%. Found: C, 58.45%; H, 5,89%.

Example 9

5-[5-(2-Propylphenyloxy)pentyloxy]-2-(hydroxymethyl)-4H-pyran-4-one (EH18900)

The compound was prepared according to scheme 1. The structure of compound ex 9 is presented below:

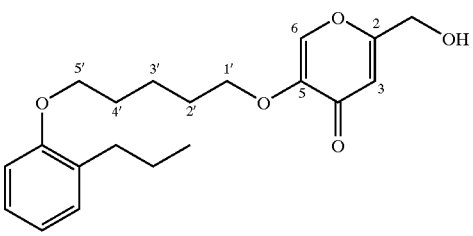

Yield: 73%; oil.
R$_f$: 0.3 (EtOAc).
IR (KBr, cm$^{-1}$): 3350, 2954, 2933, 1649, 1612, 1492, 1452, 1242, 1209, 1151, 1126.
$^1$H-NMR (CDCl$_3$, δ): 0.85 (t, J=6.9 Hz, 3H, CH$_3$), 1.45–1.95 (m, 8H, 4CH$_2$), 2.50 (t, J=7.9 Hz, 2H, CH$_2$), 3.25 (t, 6.5 Hz, 1H, OH), 3.80 (t, J=7.5 Hz, 2H, CH$_2$O), 3.90 (t, J=7.5 Hz, 2H, CH$_2$O), 4.45 (d, J=7.7 Hz, 2H, CH$_2$OH), 6.45 (s, 1H, H$_3$), 6.65–6.85 (m, 2H—Ar), 6.95–7.10 (m, 2H—Ar), 7.45 (s, 1H, H$_6$).
$^{13}$C-NMR (CDCl$_3$, δ): 14.1, 22.6, 23.0, 28.8, 29.1, 32.3, 60.8, 67.4, 69.7, 111.1, 111.8, 120.2, 126.8, 129.9, 131.2, 139.5, 147.8, 156.8, 167.5, 174.9.
Elemental analysis for C$_{20}$H$_{26}$O$_5$ Calculated: C, 69.36%; H, 7.51%. Found: C, 68.35%; H, 7.44%.

Example 10

5-[7-(3,4-Dichloro-2-propylphenyloxy)heptyloxy]-2-(hydroxymethyl)-4H-pyran-4-one (EH17701)

The compound was prepared according to Scheme 1. The structure of compound ex 10 is presented below:

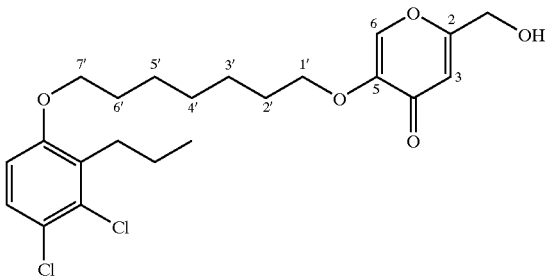

Yield: 60%; solid, mp: 62–64° C.

IR (KBr, cm$^{-1}$): 3238, 2937, 2854, 1653, 1638, 1616, 1585, 1459, 1263, 1217, 1149, 1076, 989, 949, 814.

$^1$H-NMR (CDCl$_3$, δ): 0.88 (t, J=7.3 Hz, 3H, CH$_3$), 1.19–1.55 (m, 8H, 4CH$_2$), 1.69–1.81 (m, 4H, 2CH$_2$), 2.68–2.75 (m, 2H, CH$_2$), 2.98 (br s, 1H, OH), 3.77 (t, J=6.2 Hz, 2H, CH$_2$O), 3.85 (t, J=6.5 Hz, 2H, CH$_2$), 4.41 (s, 2H, CH$_2$OH), 6.41 (s, 1H, H$_3$), 6.59 (d, J=8.9 Hz, 1H, Ar—H), 7.14 (d, J=8.8 Hz, 1H, Ar—H), 7.48 (s, 1H, H$_6$).

$^{13}$C-NMR (CDCl$_3$, δ): 14.0, 21.7, 25.7, 25.8, 28.8, 28.9, 29.0, 29.9, 60.8, 68.3, 69.6, 110.2, 118.8, 127.2, 131.6, 133.0, 139.2, 147.8, 156.0, 167.0, 174.7.

Elemental analysis for C$_{22}$H$_{28}$O$_5$Cl$_2$ Calculated: C, 59.60%; H, 6.37%. Found: C, 59.72%; H, 6.19%.

Example 11

2-(Benzyloxymethyl)-5-[5-(3,4-dichlorophenyloxy)pentyloxy]-4H-pyran-4-one (EH7701)

The compound was prepared according to Scheme 1. The structure of compound ex 11 is presented below:

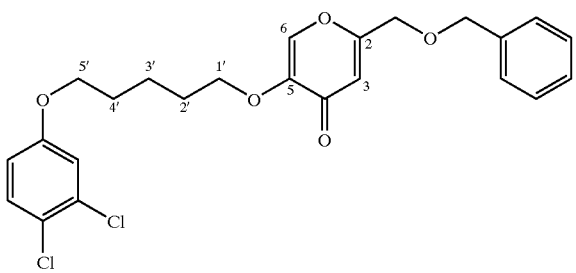

Yield: 52%; solid, mp: 82–83° C. (EtOAc-Et$_2$O).

R$_f$: 0.3 (EtOAc-Hexane).

IR (KBr, cm$^{-1}$): 3257, 3128, 3064, 2906, 1651, 1627, 1596, 1481, 1465, 1263, 999, 835, 740.

$^1$H-NMR (CDCl$_3$, δ): 1.53 (m, 2H, CH$_2$), 1.71 (m, 4H, 2CH$_2$), 3.76–3.86 (m, 4H, 2CH$_2$O), 4.21 (s, 2H, CH$_2$O), 4.52 (s, 2H, CH$_2$O), 6.41 (s, 1H, H$_3$), 6.65 (dd, J=8.9, 2.9 Hz, 1H, Ar—H), 6.89 (d, J=2.9 Hz, 1H, Ar—H), 7.17–7.34 (m, 6H, Ar—H), 7.48 (s, 1H, H$_6$).

$^{13}$C-NMR (CDCl$_3$, δ): 22.6, 28.8, 67.7, 68.4, 69.6, 73.3, 113.6, 114.6, 116,4, 123.8, 127.9, 128.3, 128.7, 130.7, 132.8, 136.9, 139.6, 148.1, 158.2, 163.9, 174.4.

Elemental analysis for C$_{24}$H$_{24}$Cl$_2$O$_5$ Calculated: C, 62.14%; H, 5.18%. Found: C, 61.88%; H, 5.13%.

Example 12

5-[5-(4-Chlorophenyloxy)pentyloxy]-4-oxo-4H-pyran-2-carboxylic acid (EH17600)

The compound was prepared according to Scheme 1. The structure of compound ex 12 is presented below:

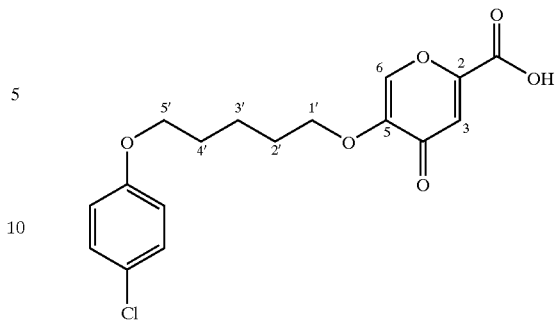

Yield: 57%; solid, mp: 154–156° C. (MeOH).

IR (KBr, cm$^{-1}$): 3402, 2947, 2876, 1732, 1602, 1602, 1578, 1493, 1477, 1283, 1242, 1209.

$^1$H-NMR (DMSO-d$_6$, δ): 1.51–1.68 (m, 2H, 2H$_{3'}$), 1.75–1.88 (m, 4H, 2H$_{2'}$, 2H$_{4'}$), 3.95 (t, J=6.3 Hz, 2H, 2H$_{1'}$ or 2H$_{5'}$), 4.05 (t, J=6.2 Hz, 2H, 2H$_{5'}$ or 2H$_{1'}$), 6.99 (s, 1H, H$_3$), 7.03 (d, J=8.7 Hz, 2H, H$_2$, H$_6$ Ar—H), 7.38 (d, J=8.7 Hz, 2H, H$_3$, H$_5$ Ar—H), 8.35 (s, 1H, H$_6$).

$^{13}$C-NMR (DMSO-d$_6$, δ): 21.9, 28.2, 67.7, 68.5, 116.1, 116.9, 124.0, 129.1, 140.6, 148.4, 152.2, 157.9, 160.7, 173.7.

Elemental analysis for C$_{17}$H$_{17}$O$_6$Cl Calculated: C, 57.84%; H, 4.82%. Found: C, 57.61%; H, 5.01%.

Example 13

5-[5-(3-Chlorophenyloxy)pentyloxy]-4-oxo-4H-pyran-2-carboxylic acid (EH15700)

The compound was prepared according to Scheme 1. The structure of compound ex 13 is presented below:

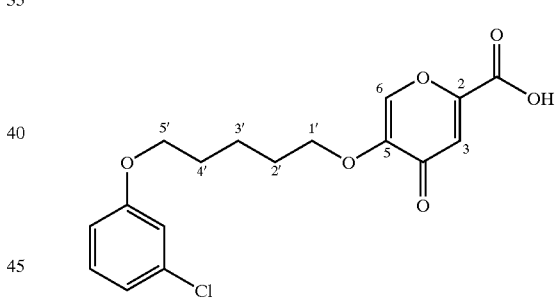

Yield: 60%; solid, mp: 160–161° C. (MeOH).

IR (KBr, cm$^{-1}$): 3439, 2941, 2912, 1733, 1635, 1601, 1576, 1284, 1232, 1209.

$^1$H-NMR (DMSO-d$_6$, δ): 1.56–1.64 (m, 2H, 2H$_{3'}$), 1.73–1.83 (m, 4H, 2H$_{2'}$, 2H$_{4'}$), 3.76 (t, J=6.2 Hz, 2H, 2H$_{1'}$ or 2H$_{5'}$), 3.88 (t, J=6.2 Hz, 2H, 2H$_{5'}$ or 2H$_{1'}$), 6.91–6.97 (m, 4H, H$_2$, H$_4$, H$_6$ Ar—H, H$_3$), 7.34 (t, J=7.9 Hz, 1H, H$_5$ Ar—H), 8.31 (s, 1H, H$_6$).

$^{13}$C-NMR (DMSO-d$_6$, δ): 21.9, 28.1, 67.7, 68.8, 113.5, 114.3, 116.9, 120.3, 130.7, 133.6, 140.5, 148.5, 152.3, 159.5, 160.7, 172.8.

Elemental analysis for C$_{17}$H$_{17}$O$_6$Cl Calculated: C, 57.84%; H, 4.82%. Found: C, 58.05%; H, 5.09%.

Example 14

5-[5-(2-Propylphenyloxy)pentyloxy]-4-oxo-4H-pyran-2-carboxylic acid (EH26900)

The compound was prepared according to scheme 1. The structure of compound ex 14 is presented below:

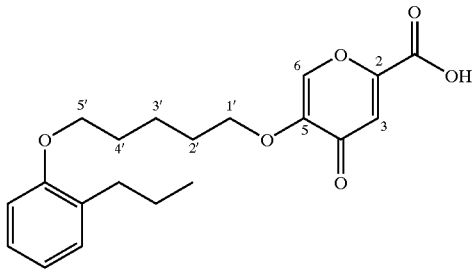

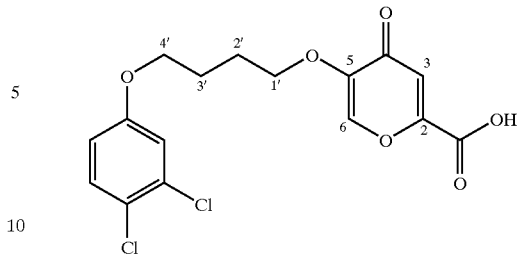

Yield: 56%; solid, mp: 145–146° C. (EtOAc).

IR (KBr, cm$^{-1}$): 3443, 2957, 2932, 2573, 2437, 1732, 1635, 1601, 1572, 1242, 1207, 935, 760.

$^1$H-NMR (DMSO-$d_6$, $\delta$): 0.86 (t, J=7.4 Hz, 3H, CH$_3$), 1.00–1.21 (m, 4H, 2CH$_2$), 1.43–1.82 (m, 4H, 2CH$_2$), 2.47–2.55 (m, 2H, CH$_2$—Ar), 3.85–4.00 (m, 4H, 2CH$_2$O), 6.79–6.93 (m, 3H, H$_3$, 2H—Ar), 7.08–7.18 (m, 2H—Ar), 8.20 (s, 1H, H$_6$).

$^{13}$C-NMR (DMSO-$d_6$, $\delta$): 14.0, 22.3, 22.7, 28.3, 28.6, 31.8, 67.3, 69.0, 111.5, 117.0, 120.1, 127.1, 129.7, 130.2, 140.7, 148.7, 152.8, 156.5, 161.0, 173.0.

Elemental analysis for $C_{20}H_{24}O_6$ Calculated: C, 66.65%; H, 6.71%. Found: C, 66.34%; H, 6.65%

Yield: 57%; solid, mp: 182–183° C. (MeOH).

IR (KBr, cm$^{-1}$): 3452, 3107, 3076, 2972, 2918, 2875, 1735, 1618, 1598, 1562, 1475, 1249, 974, 788.

$^1$H-NMR (DMSO-$d_6$, $\delta$): 1.55–1.75 (m, 4H, 2H$_{2'}$, 2H$_{3'}$), 3.75 (t, J=6.2 Hz, 2H, 2H$_{1'}$ or 2H$_{4'}$), 3.88 (t, J=6.2 Hz, 2H, 2H$_{4'}$ or 2H$_{1'}$), 6.74 (s, 1H, H$_3$), 6.79 (dd, J=8.9, 2.9 Hz, 1H, H$_6$ Ar—H), 7.05 (d, J=2.9 Hz, 1H, H$_2$ Ar—H), 7.33 (d, J=8.9 Hz, 1H, H$_5$ Ar—H), 8.11 (s, 1H, H$_6$).

$^{13}$C-NMR (DMSO-$d_6$, $\delta$): 25.1, 67.9, 68.7, 115.5, 116.4, 117.0, 122.3, 130.9, 131.6, 140.7, 148.6, 152.5, 158.2, 160.9, 172.9.

Elemental analysis for $C_{16}H_{14}O_6Cl_2$ Calculated: C, 51.47%; H, 3.75%. Found: C, 51.23%; H, 3.87%.

Example 15

5-[5-(3,4-Dichlorophenyloxy)pentyloxy]-4-oxo-4H-pyran-2-carboxylic acid (EH6600)

The compound was prepared according to Scheme 1. The structure of compound ex 15 is presented below:

Example 17

5-[5-(3,4-Dichloro-2-propylphenyloxy)pentyloxy]-4-oxo-4H-pyran-2-carboxylic acid (EH27900)

The compound was prepared according to Scheme 1. The structure of compound ex 17 is presented below:

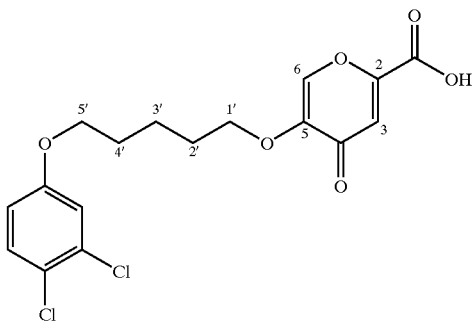

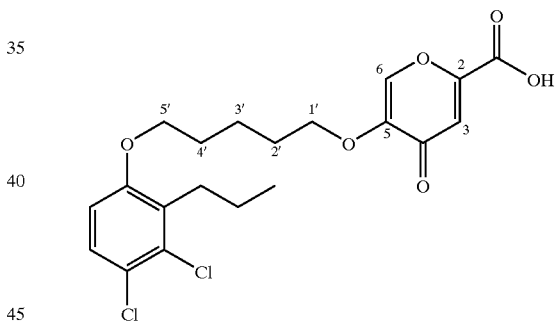

Yield: 55%; solid, mp: 159–161° C. (EtOAc/Hexane)

IR (KBr, cm$^{-1}$): 3437, 2874, 2345, 1732, 1637, 1602, 1569, 1471, 1282, 1207.

$^1$H-NMR (DMSO-$d_6$, $\delta$): 1.49–1.55 (m, 2H, 2H$_{3'}$), 1.68–1.77 (m, 4H, 2H$_{2'}$, 2H$_{4'}$), 3.86 (t, J=6.3 Hz, 2H, 2H$_{1'}$ or 2H$_{5'}$), 3.99 (t, J=6.3 Hz, 2H, 2H$_{5'}$ or 2H$_{1'}$), 6.89 (s, 1H, H$_3$), 6.94 (dd, J=8.7, 3.5 Hz, 1H, H$_6$ Ar—H), 7.21 (d, J=3.5 Hz, 1H, H$_2$ Ar—H), 7.48 (d, J=8.7 Hz, 1H, H$_5$ Ar—H), 8.26 (s, 1H, H$_6$).

$^{13}$C-NMR (DMSO-$d_6$, $\delta$): 21.7, 27.8, 68.0, 68.6, 115.3, 116.0, 116.7, 121.9, 130.7, 131.3, 140.4, 148.4, 152.2, 157.9, 160.7, 172.7.

Elemental analysis for $C_{17}H_{16}O_6Cl_2$ Calculated: C, 52.73%; H, 4.16%. Found: C, 52.59%; H, 4.21%.

Example 16

5-[4-(3,4-Dichlorophenyloxy)butyloxy]-4-oxo-4H-pyran-2-carboxylic acid (EH20700)

The compound was prepared according to Scheme 1. The structure of compound ex 16 is presented below:

Yield: 55%; solid, mp: 155–156° C. (MeOH-Acetone).

IR (KBr, cm$^{-1}$): 3448, 3090, 2958, 2870, 2570, 2447, 1736, 1635, 1603, 1577, 1452, 1263, 1246, 1032, 935, 758.

$^1$H-NMR (DMSO-$d_6$, $\delta$): 0.90 (t, J=7.3 Hz, 3H, CH$_3$), 1.38–1.62 (m, 4H, 2CH$_2$), 1.81–1.95 (m, 4H, 2CH$_2$), 2.73 (t, J=8.0 Hz, 2H, CH$_2$—Ar), 3.88 (t, J=6.2 Hz, 2H, 2CH$_2$O), 3.99 (t, J=6.1 Hz, 2H, 2CH$_2$O), 6.91 (s, 1H, H$_3$), 7.00 (d, J=7.1 Hz, 1H, Ar—H), 7.41 (d, J=7.5 Hz, 1H, Ar—H), 8.28 (s, 1H, H$_6$).

$^{13}$C-NMR (DMSO-$d_6$, $\delta$): 13.7, 21.3, 21.9, 27.9, 28.1, 29.4, 68.0, 68.7, 111.5, 116.8, 123.0, 127.8, 130.5, 131.0, 140.4, 148.5, 152.3, 155.9, 160.7, 172.7.

Elemental analysis for $C_{20}H_{22}O_6Cl_2$ Calculated: C, 55.96%; H, 5.17%. Found: C, 56.03%; H, 5.10%.

Example 18

5-[5-(2-Ethyloxyphenyloxy)pentyloxy]-4-oxo-4H-pyran-2-carboxylic acid (EH4701)

The compound was prepared according to Scheme 1. The structure of compound ex 18 is presented below:

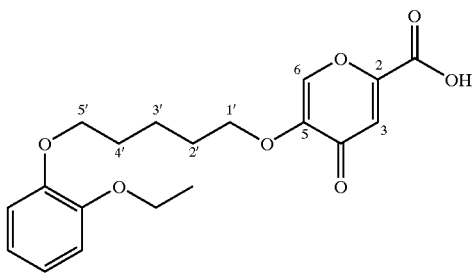

Yield: 75%; solid, mp: 141–142° C.

IR (CHCl$_3$, cm$^{-1}$): 3068, 2875, 1732, 1637, 1602, 1575, 1253, 1211.

$^1$H-NMR (DMSO, δ): 1.47 (t, J=6.9 Hz, 3H, CH$_3$), 1.71–1.78 (m, 2H, CH$_2$), 1.82–2.00 (m, 4H, 2CH$_2$), 4.02–4.21(m, 6H, 3CH$_2$), 7.00–7.15 (m, 5H, H$_3$, 4H, Ar—H), 8.45 (s, 1H, 1H$_6$).

$^{13}$C-NMR (DMSO-d$_6$, δ): 14.5, 21.8, 27.9, 28.2, 63.6, 68.1, 68.7, 113.7, 116.6, 120.7, 140.3, 148.2, 148.3, 148.4, 152.2, 160.6, 172.2.

Elemental analysis for C$_{19}$H$_{22}$O$_7$ Calculated: C, 62.97%; H, 6.12%. Found: C, 62.75%; H, 6.05%.

Example 19

N-Benzyl-5-[5-(4-Chlorophenyloxy)pentyloxy]-4-oxo-4H-pyran-2-carboxamide (EH28900)

The compound was prepared according to Scheme 1. The structure of compound ex 19 is presented below:

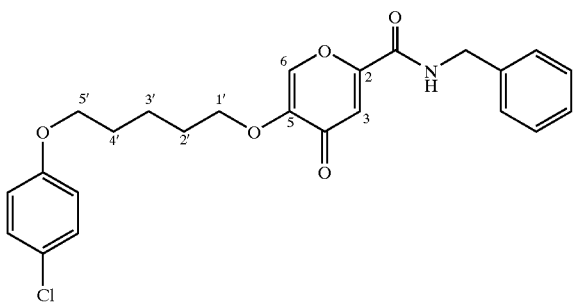

Yield: 56%; solid, mp: 125–126° C. (MeOH/Et$_2$O).

R$_f$: 0.3 (EtOAc).

IR (KBr, cm$^{-1}$): 3423, 2947, 1732, 1637, 1602, 1569, 1469, 1282, 1207, 1122, 864.

$^1$H-NMR (CDCl$_3$, δ):1.35–1.95 (m, 6H, 3CH$_2$), 3.75–3.95 (m, 4H, 2CH$_2$O), 4.45 (d, J=7.5 Hz, 2H, CH$_2$N), 6.72 (d, J=9.0 Hz, 2H, Ar—H), 7.10–7.35 (m, 8H, H$_3$, 7H, Ar—H), 7.45 (s, 1H, H$_6$).

$^{13}$C-NMR (CDCl$_3$, δ): 22.2, 26.7, 28.8, 29.6, 32.2, 62.6, 67.8, 115.6, 127.5, 128.0, 128.8, 129.2, 157.5.

Elemental analysis for C$_{24}$H$_{24}$ClNO$_5$ Calculated: C, 65.23%; H, 5.44%; N, 3.17%. Found: C, 64.84%; H, 5.64%; N, 3.12%.

Example 20

(E)-3-[5-(4-Chlorophenyloxy)pentyloxy]-6-(hydroxymethyl)-2(propen-1-yl)-4H-pyran-4-one (EH26101)

The compound was prepared according to Scheme 2. The structure of compound ex 20 is presented below:

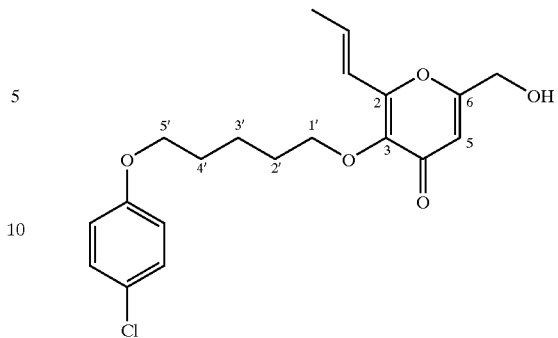

Yield: 75%; solid, mp: 84–85° C.

R$_f$: 0.3 (EtOAc/Hexane).

IR (KBr, cm$^{-1}$): 3350, 3012, 2943, 1718, 1654, 1641, 1596, 1560, 1492, 1473, 1436, 1286, 1244, 1217, 1197, 1170, 1153.

$^1$H-NMR (CDCl$_3$, δ): 1.48–1.79 (m, 6H, 3CH$_2$), 1.85 (d, J=5.0 Hz, 3H, CH$_3$), 3.86 (t, J=6.3 Hz, 2H, CH$_2$O), 4.00 (t, J=6.3 Hz, 2H, CH$_2$O), 4.40 (s, 2H, CH$_2$OH), 6.41 (s, 1H, H$_5$), 6.48–6.53 (m, 2H, —CH=), 6.70 (d, J=9.0 Hz, 2H, H$_2$, H$_6$ Ar—H), 7.14 (d, J=9.0 Hz, 2H, H$_3$, H$_5$ Ar—H)

$^{13}$C-NMR (CDCl$_3$, δ): 18.7, 22.3, 28.7, 29.5, 60.6, 67.9, 72.4, 111.9, 115.6, 118.5, 125.1, 129.1, 134.5, 141.2, 154.8, 157.5, 166.1, 176.6.

Elemental analysis for C$_{20}$H$_{23}$ClO$_5$ Calculated: C, 63.41%; H, 6.07%. Found: C, 64.26%; H, 6.03%.

Example 21

(E)-3-[5-(3-Chlorophenyloxy)pentyloxy]-6-(hydroxymethyl)-2-(propen-1-yl)-4H-pyran-4-one (EH16201)

The compound was prepared according to Scheme 2. The structure of compound ex 21 presented below:

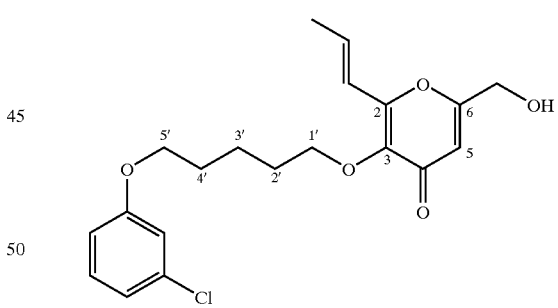

Yield: 77%; solid, mp: 50–51° C. (Et$_2$O).

R$_f$: 0.3 (EtOAc/Hexane).

IR (CHCl$_3$, cm$^{-1}$): 3392, 3018, 2943, 1654, 1643, 1595, 1469, 1436, 1284, 1215.

$^1$H-NMR (CDCl$_3$, δ): 1.45–1.81 (m, 6H, 3CH$_2$), 1.85 (d, J=5.1 Hz, 3H, CH$_3$), 3.88 (t, J=6.3 Hz, 2H, CH$_2$O), 3.98 (t, J=7.1 Hz, 2H, CH$_2$O), 4.41 (s, 2H, CH$_2$OH), 6.36 (s, 1H, H$_5$), 6.42–6.52 (m, 2H, —CH=), 6.68 (dd, J=7.1, 1.3 Hz, 1H, Ar—H), 6.81–6.86 (m, 2H, Ar—H), 7.11 (t, J=8.3 Hz, 1H, Ar—H).

$^{13}$C-NMR (CDCl$_3$, δ): 18.9, 22.4, 28.9, 29.6, 60.9, 68.0, 72.5, 112.2, 113.0, 114.8, 118.7, 120.7, 130.1, 134.5, 134.8, 141.4, 154.8, 159.8, 165.9, 176.7.

Elemental analysis for $C_{20}H_{23}ClO_5$ Calculated: C, 63.41%; H, 6.12%. Found: C, 62.64%; H, 6.09%.

Example 22

(E)-(3-[5-(3,4-Dichlorophenyloxy)pentyloxy]-6-(hydroxymethyl)-2-(propen-1-yl)-4H-pyran-4-one (EH30101)

The compound was prepared according to Scheme 2. The structure of compound ex 22 is presented below:

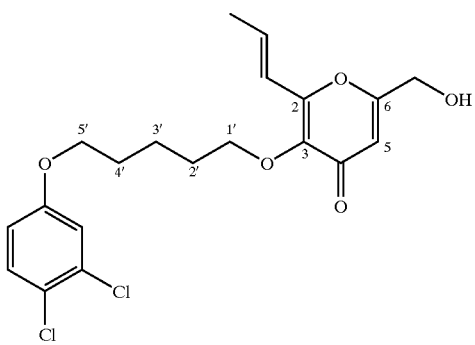

Yield: 77%; soild, mp: 100–101° C. (EtOc/Hexane)

$R_f$: 0.3 (EtOAc/Hexane).

IR (KBr, cm$^{-1}$): 3220, 2947, 2850, 2765, 2360, 2343, 1658, 1643, 1600, 1568, 1541, 1508, 1481, 1463, 1438, 1234, 1207, 1181.

$^1$H-NMR (CDCl$_3$, δ): 1.45–1.81 (m, 6H, 3CH$_2$), 1.86 (d, J=5.0 Hz, 3H, CH$_3$), 2.97 (t, J=7.0 Hz, 1H, OH), 3.85 (t, J=7.0 Hz, 2H, CH$_2$O), 4.02 (t, J=7.0 Hz, 2H, CH$_2$O), 4.41 (d, J=7.0 Hz, 2H, CH$_2$OH), 6.35 (s, 1H, H$_5$), 6.49–6.55 (m 2H, —CH═), 6.67 (dd, J=9.0, 3.0 Hz, 1H, H$_6$ Ar—H), 6.91 (d, J=3.0 Hz, 1H, H$_2$ Ar—H), 7.23 (d, 9.0 Hz, 1H, H$_5$ Ar—H).

$^{13}$C-NMR (CDCl$_3$, δ)18.6, 22.2, 28.6, 29.4, 60.6, 68.2, 72.2, 164, 114.3, 116.2, 118.5, 123.5, 130.4, 132.5, 134.1, 141.3, 154.4, 157.9, 164.9, 176.2.

Elemental analysis for $C_{20}H_{22}O_5Cl_2$ Calculated: C, 58.12%; H, 5.37%. Found: C, 58.02%; H, 5.39%.

Example 23

(E)-3-[5-(3,4-Dichloro-2-propylphenyoxy)pentyloxy]-6-(hydroxymethyl)-2-(propen-1-yl)-4H-pyran-4-one (EH31101)

The compound was prepared according to Scheme 2. The structure of compound ex 23 is presented below:

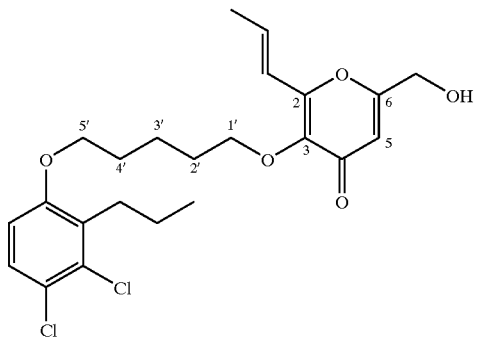

Yield: 75%; solid, mp: 75–76° C. (Et$_2$O).

$R_f$: 0.3 (EtOAc-Hexane).

IR (KBr, cm$^{-1}$): 3222, 2929, 1660, 1598, 1456, 1442, 1261, 1234, 1097, 1058, 962.

$^1$H-NMR (CDCl$_3$, δ): 0.88 (t, J=7.3 Hz, 3H, CH$_3$), 1.41–1.86 (m, 8H, 4CH$_2$), 1.86 (d, J=5.1 Hz, 3H, CH$_3$), 2.72 (m, 3H, OH, CH$_2$—Ar), 3.88 (t, J=6.2 Hz, 2H, CH$_2$O), 4.01 (t, J=6.4 Hz, 2H, CH$_2$O), 4.42 (d, J=4.7 Hz, 2H, CH$_2$OH), 6.34 (s, 1H, 1H$_5$), 6.51 (m, 2H, —CH═), 6.62 (d, J=8.8 Hz, 1H, Ar—H), 7.15 (d, J=8.8 Hz, 1H, Ar—H).

$^{13}$C-NMR (CDCl$_3$, δ): 14.1, 18.8, 21.8, 22.4, 28.9, 29.6, 30.0, 61.0, 68.3, 72.4, 110.2, 112.4, 118.7, 124.1, 127.2, 131.7, 132.7, 134.1, 142.5, 154.5, 156.1, 164.8, 176.2.

Elemental analysis for $C_{23}H_{28}O_5Cl_2$ Calculated: C, 60.66%; H, 6.20%. Found: C, 60.44%; H, 6.24%.

Example 24

(E)-6-(Hydroxymethyl)-2-(propen-1-yl)-3-[5-(2-propylphenyloxy)pentyloxy]-4H-pyran-4-one (EH9301)

The compound was prepared according to Scheme 2. The structure of compound ex 24 is presented below:

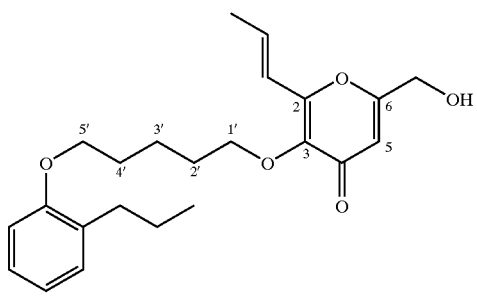

Yield: 75%; solid, mp: 67–68° C. (EtOAc-Et$_2$O).

$R_f$: 0.3 (EtOAc/Hexane).

IR (CHCl$_3$, cm$^{-1}$): 3367, 2954, 2868, 1654, 1641, 1601, 1452, 1240, 1191, 968.

$^1$H-NMR (CDCl$_3$, δ): 1.01 (t, J=7.4 Hz, 3H, CH$_3$), 1.51–1.70 (m, 4H, 2CH$_2$), 1.75–1.90 (m, 4H, 2CH$_2$), 1.90 (d, J=5.7 Hz, 3H, CH$_3$), 2.66 (t, J=7.8 Hz, 2H, CH$_2$—Ar), 3.96 (t, J=7.5 Hz, 2H, CH$_2$O), 4.07 (t, J=7.7 Hz, 2H, CH$_2$O), 4.56 (s, 2H, CH$_2$OH), 6.42 (s, 1H, H$_5$), 6.47–6.58 (m, 2H, —CH═), 6.85–6.97 (m, 2H, Ar—H), 7.15–7.25 (m, 2H, Ar—H).

$^{13}$C-NMR (CDCl$_3$, δ): 14.1, 18.9, 22.6, 23.1, 29.2, 29.7, 32.4, 60.9, 67.6, 72.8, 111.1, 112.1, 118.7, 120.2, 126.8, 129.9, 131.2, 134.8, 141.4, 155.2, 156.9, 176.3.

Elemental analysis for $C_{23}H_{30}O_5$ Calculated: C, 71.48%; H, 7.82%. Found: C, 70.92%; H, 7.81%.

Example 25

(E)-3-[-5-(4-Chlorophenyloxy)pentyloxy]-2-(propen-1-yl)-4-oxo-4H-pyran-6-carboxylic acid (EH17401)

The compound was prepared according to Scheme 2. The structure of compound ex 25 is presented below:

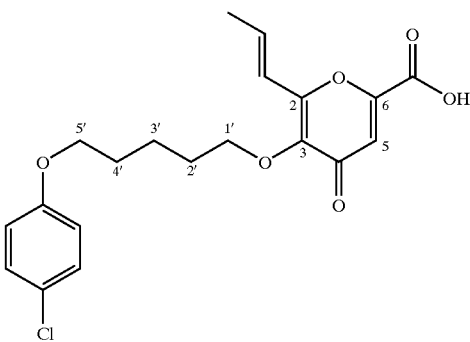

Yield: 55%; solid, mp: 136–137° C. (EtOAc-$Et_2O$).
$R_f$: 0.3 (EtOAc).
IR ($CHCl_3$, $cm^{-1}$): 3076, 2943, 2914, 2871, 1732, 1647, 1629, 1596, 1581, 1541, 1492, 1442, 1286, 1244.
$^1$H-NMR ($CDCl_3$, δ): 1.48–1.60 (m, 2H, $CH_2$), 1.69–1.78 (m, 4H, $2CH_2$), 1.87 (d, J=6.8 Hz, 3H, $CH_3$), 3.83 (t, J=6.3 Hz, 2H, $CH_2O$), 4.06 (t, J=6.5 Hz, 2H, $CH_2O$), 6.53 (dd, J=15.8, 1.5 Hz, 1H, —CH=), 6.75 (d, J=9.0 Hz, 2H, Ar—H), 6.76–6.95 (m, 1H, —CH=), 7.10 (d, J=9.0 Hz, 2H, Ar—H) 7.26 (s, 1H, $H_5$), 7.71 (br s, 1H, COOH).
$^{13}$C-NMR ($CDCl_3$, δ): 16.2, 19.1, 22.4, 28.9, 29.7, 68.1, 72.7, 115.8, 118.2, 118.5, 125.4, 129.3, 138.1, 142.9, 151.4, 156.7, 157.6, 161.1, 177.1.
Elemental analysis for $C_{20}H_{21}O_6Cl$ Calculated: C, 61.14%; H, 5.35%. Found: C, 60.93%; H, 5.35%.

Example 26

(E)-3-[5-(3-Chlorophenyloxy)pentyloxy]-2-(propen-1-yl)-4-oxo-4H-pyran-6-carboxylic acid (EH18401)

The compound was prepared according to Scheme 2. The structure of compound ex 26 is presented below:

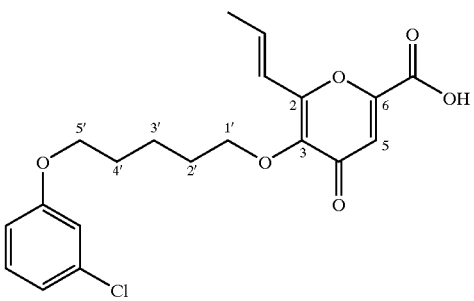

Yield: 57%; solid, mp: 116–117° C. (EtOAc-$Et_2O$)
$R_f$: 0.3 (EtOAc).
IR ($CHCl_3$, $cm^{-1}$): 3070, 2945, 2873, 1735, 1637, 1595, 1579, 1544, 1469, 1440, 1385, 1307, 1245, 1182.

$^1$H-NMR ($CDCl_3$, δ): 1.76–1.82 (m, 2H, $CH_2$), 1.88–1.96 (m, 4H, $2CH_2$), 2.09 (d, J=5.9 Hz, 3H, $CH_3$), 4.07 (t, J=6.1 Hz, 2H, $CH_2O$), 4.28 (t, J=6.6 Hz, 2H, $CH_2O$), 6.74 (dd, J=18.0, 1.5 Hz, 1H, —CH=), 6.92–7.08 (m, 4H, 1H, —CH=, 3H Ar—H,), 7.28 (t, J=8.5 Hz, 1H, Ar—H), 7.47 (s, 1H, $H_5$), 8.12 (br s, 1H, COOH).
$^{13}$C-NMR ($CDCl_3$, δ): 18.9, 22.2, 28.7, 29.5, 67.8, 72.5, 112.8, 114.6, 118.0, 118.3, 120.5, 130.0, 134.6, 137.9, 142.7, 151.2, 156.5, 159.6, 160.9, 176.9.
Elemental analysis for $C_{20}H_{21}O_6Cl$ Calculated: C, 61.14%; H, 5.35%. Found: C, 60.57%; H, 5.34%.

Example 27

(E)-3-[5-(3,4-Dichlorophenyloxy)pentyloxy]-2-(propen-1-yl)-4-oxo-4H-pyran-6-carboxylic acid (EH10501)

The compound was prepared according to Scheme 2. The structure of compound ex 27 is presented below:

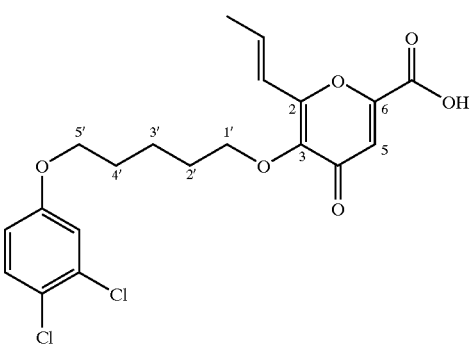

Yield: 58%; solid, mp: 118–119° C. (EtOAc-$Et_2O$)
$R_f$: 0.3 (EtOAc).
IR ($CHCl_3$, $cm^{-1}$): 3018, 2945, 2873, 1732, 1645, 1633, 1593, 1546, 1469, 1442.
$^1$H-NMR ($CDCl_3$, δ): 1.56–1.68 (m, 2H, $CH_2$), 1.72–1.82 (m, 4H, $2CH_2$), 1.91 (d, J=6.8 Hz, 3H, $CH_3$), 3.88 (t, J=6.2 Hz, 2H, $CH_2O$), 4.09 (t, J=7.1 Hz, 2H, $CH_2O$), 6.57 (dd, J=14.9, 1.5 Hz, 1H, —CH=), 6.67 (dd, J=8.8, 2.9 Hz, 1H, Ar—H), 6.75–6.86 (m, 1H, —CH=), 6.91 (d, J=2.8 Hz, 1H, Ar—H), 7.18 (d, J=8.8 Hz, 1H, Ar—H), 7.21 (s, 1H, $H_5$), 7.21 (br s, 1H, COOH).
$^{13}$C-NMR ($CDCl_3$, δ): 19.1, 22.3, 28.7, 29.6, 68.3, 72.5, 114.5, 116.2, 118.1, 118.5, 122.9, 127.5, 130.5, 137.9, 142.9, 151.7, 156.5, 158.1, 161.1, 176.5.
Elemental analysis for $C_{20}H_{20}Cl_2O_6$ Calculated: C, 56.22%; H, 4.72%. Found: C, 55.58%; H, 4.61%.

Example 28

(E)-3-[5-(3,4-Dichloro-2-propylphenyloxy)pentyloxy]-2-(propen-1-yl)-4-oxo-4H-pyran-6-carboxylic acid (EH2250 1)

The compound was prepared according to Scheme 2. The structure of compound ex 28 is presented below:

Yield: 57%; solid, mp: 161–162° C. (EtOAc-Et$_2$O).

R$_f$: 0.2 (EtOAc).

IR (CHCl$_3$, cm$^{-1}$): 3423, 3082, 2958, 2931, 1726, 1649, 1631, 1578, 1549, 1454, 1261, 1201, 1182, 968.

$^1$H-NMR (DMSO-d$_6$, δ): 0.72 (t, J=7.5 Hz, 3H, CH$_3$), 1.23–1.43 (m, 4H, 2CH$_2$), 1.53–1.63 (m, 4H, 2CH$_2$), 1.76 (d, J=5.2 Hz, 3H, CH$_3$), 2.56 (t, J=7.4 Hz, 2H, CH$_2$—Ar), 3.82–3.91 (m, 4H, 2CH$_2$O), 6.38–6.55 (m, 2H, —CH=), 6.69 (s, 1, H$_5$), 6.82 (d, J=8.8 Hz, 1H, Ar—H), 7.26 (d, J=8.8 Hz, 1H, Ar—H).

$^{13}$C-NMR (DMSO-d$_6$, δ): 13.8, 18.4, 21.3, 22.1, 28.2, 28.9, 29.5, 68.2, 71.7, 111.6, 117.5, 118.3, 122.7, 127.8, 130.6, 131.3, 135.5, 142.9, 151.7, 153.8, 156.1, 160.8, 174.8.

Elemental analysis for C$_{23}$H$_{26}$Cl$_2$O$_6$ Calculated: C, 58.86%; H, 5.58%. Found: C, 58.77%; H, 5.36%.

Example 29

(E)-2-(Propen-1-yl)-3-[5-(2-propylphenyloxy) pentyloxy]-4-oxo-4H-pyran-6-carboxylic acid (EH15301)

The compound was prepared according to Scheme 2. The structure of compound ex 29 is presented below:

Yield: 53%; solid, mp: 145–146° C. (c-Hex).

R$_f$: 0.4 (EtOAc).

IR (CHCl$_3$, cm$^{-1}$): 3063, 2957, 2870, 2559, 1736, 1637, 1585, 1493, 1242, 1184, 970, 908.

$^1$H-NMR (CDCl$_3$, δ): 0.78 (t, J=7.4 Hz, 3H, CH$_3$), 1.40–1.51 (m, 4H, 2CH$_2$), 1.65–1.76 (m, 4H, 2CH$_2$), 1.83 (d, J=6.3 Hz, 3H, CH$_3$), 2.44 (t, J=7.9 Hz, 2H, CH$_2$—Ar), 3.84 (t, J=5.9 Hz, 2H, CH$_2$O), 4.04 (t, J=5.1 Hz, 2H, CH$_2$O), 6.46–6.54 (m, 1H, —CH=), 6.65–6.77 (m, 3H, 1H, —CH=, 2H, Ar—H,), 6.96–7.03 (m, 2H, Ar—H), 7.21 (s, 1H, H$_5$).

$^{13}$C-NMR (CDCl$_3$, δ): 14.2, 19.2, 22.7, 23.2, 29.2, 29.8, 32.5, 67.6, 72.9, 111.2, 118.3, 118.7, 120.3, 126.9, 130.0, 131.3, 138.0, 143.1, 152.0, 156.7, 157.0, 162.0, 177.1.

Elemental analysis for C$_{23}$H$_{28}$O$_6$ Calculated: C, 68.98%; H, 7.05%. Found: C, 68.19%; H, 6.97%.

Additionally, it has been carried out the synthetic route previously reported [EP 0 304 221] that leads to the triazole L-651582:

Yield: 55%; solid, mp: 202–204° C. (MeOH).

R$_f$: 0.3 (EtOAc).

$^1$H-NMR (CD$_3$OD, δ): 5.37 (s, 2H, NH$_2$), 5.48 (s, 2H, CH$_2$—N), 5.59 (br s, 1H, NH$_2$), 6.78 (br s, 1H, NH$_2$), 7.24 (s, 2H, H$_{2,6}$), 7.42 (d, J=8.5 Hz, 2H, H$_{3',5'}$), 7.69 (d, J=8.5 Hz, 2H, H$_{2',6'}$).

$^{13}$C-NMR (CD$_3$OD, δ): 48.9, 128.4 (2C), 130.6 (2C), 132.1 (2C), 133.2, 135.2, 138.0, 141.0, 142.1, 146.8, 192.3.

MS (EI, 70 eV): 425 (M), 379, 353, 199, 139 (100%), 98, 63, 55.

Elemental analysis for C$_{17}$H$_{12}$O$_2$N$_5$Cl$_3$ Calculated: C, 48.05%; H, 2.82%; N, 16.47%. Found: C, 48.08%; H, 3.40%; N, 15.83%.

Example 30

Pharmacology

This example discloses the various assay conditions used to illustrate the biological activity of the compounds.

Methods

A series of tests was designed to screen the various compounds and evaluate their direct effect on small GTPases activities as well as their anti-proliferative and anti-tumor potential. Compound L651582 CAI (carboxyamidotriazole) was included as a positive control for G-protein mediated signalling inhibition (Kohn et al., J. Natl. Cancer Inst., 1990).

a) Cell Culture and Cytotoxicity Assay

Four human tumoral cell lines, namely HCT116 colon adenocarcinoma, H460 lung carcinoma, MCF-7 and MDA-MB-231 breast carcinoma cell lines, and three immortalized but non tumorigenic cell lines, namely NIH3T3 mouse fibroblasts and human breast-derived MCF10-A and MRC-5 were purchased at ATCC and cultured according to their recommendations. In order to determine the cytotoxicity associated with one compound, a microculture tetrazolium assay (MTT), as described by Carmichael et al (Cancer Res, 1996) with modifications, was used. Briefly, 5.10$^3$ or 2.10$^4$ cells were seeded per well in 24-well plates 24 hours before drug addition. Cells were treated with 0, 1, 10, 17.5, 25 and 5 μM of compound solubilized in DMSO, adjusting the total volume of DMSO (Dimethylsulfoxide) to 1%. Forty-eight hours or 6 days after treatment, the medium was replaced by PBS containing 0.5 mg/ml MTT (Sigma) and cells were incubated for 3 more hours at 37° C. before solubilization of formazan crystals in 100% DMSO. Absorbance was measured using a spectrophotometer at a wavelength of 550 nm. Cell surviving fraction and 50% inhibitory concentration were calculated. All assays were performed in triplicate.

b) Anchorage-independent Growth Assay

In order to evaluate the effect of the compounds on the capacity of tumor cells to grow without anchorage, HCT116 cells were seeded either in agar or in Matrigel (BD, France). For 3D growth experiment in soft agar in 24-well plates, $5.10^3$ HCT 116 cells were resuspended in 250 μl of complete medium containing 0.3% soft-agar (Difco) and different concentrations of compound (0.1, 1, 10, 17.5, 25 and 50 μM). Cells were then poured on a solidified layer of medium containing 0.5% of soft-agar plus the compound at the same concentration than in the upper layer. Cells were incubated at 37° C. for 1 week before they were analysed using a phase contrast microscope (Nikon). For 3D growth experiment in Matrigel, $10^4$ HCT116 cells were resuspended in 300 μl of complete medium containing 5 mg/ml Matrigel (BD, France) and different concentrations of compound (0.1, 1, 10, 17.5, 25 and 50 μM), and poured in 24-well plates. After solidification at 37° C. for 15 min., complete medium containing the compound was added to each well. Cells were incubated for 1 week before they were collected using Matrisperse (BD, France) according to the manufacturer's instructions. After recovery, alive cells were counted with trypan blue exclusion.

c) Ras/Rac-dependant Signaling Pathway Analysis

The impact of the compounds on Ras and Rac signaling pathways was analysed with two reporter systems described by Imler (Nature 1988) and Lin (Science, 1995) respectively on one hand, and by a colony formation assay in the presence of constitutively activated Ras (RasV12) and Rac (RacV12) on the other hand. For this latter experiment, fifty percent confluent NIH3T3 cells in a 10 cm diameter petri dish were transfected with 0.5 μg pSV2-RasV12 or 0.5 μg pEXV RacV12 plasmids plus 100 ng of pSV2-neomycin plasmid using Lipofectamine-Plus reagent (Invitrogen) according to the manufacturer's instructions. Forty-eight hours later, cells were trypsinised, splitted to 1/3, and incubated in the presence of complete medium supplemented with 400 μg/ml geneticin (Invitrogen) and different doses of compound (1, 10, 17.5, 25 and 50 μM) until emerging resistant clones appear (2–3 weeks). The medium was renewed every 3 days. Colonies with a minimum of 50 cells were counted after staining with Fuschin 2%.

d) Migration and Matrigel Invasion Assay

Chemoinvasion assay was performed in Boyden chamber as described by Albini et al (Cancer Res, 1987) with some modifications. Polycarbonate membranes with 8μm pores were coated with matrigel (125 μg/cm²) at room temperature for 48 h. Two hours before experiments, the matrix was dehydrated with serum-free medium containing 0.1% BSA.

One day after seeding, $10^6$ MDA-MB-231 cells were treated overnight with different concentrations of compounds (1, 10, 17.5, 25 and 50 μM). Cells were collected with Versene (Invitrogen), counted with trypan blue exclusion, rinsed twice in serum-free medium containing 0.1% BSA and resuspended in serum-free medium containing 0.1% BSA plus the appropriate concentration of compound. $10^5$ treated cells were placed in the upper chamber. Medium containing 10% of FBS plus the appropriate concentration of compound was placed in the lower chamber as a chemoattractant. The Boyden chamber was incubated 6 hours at 37° C. before the cells were fixed and stained with Diff-Quick (Dade-Berhing). Cells on the upper part of the filters were removed using a cotton swab. Cells on the underside of the filters were visualised and counted under light microscope. The migration assay was performed the same way, using non-coated filters.

e) Gelatin Zymography

The activity of the metalloproteases MMP-2 and MMP-9 was assayed using gelatinolytic zymography according to Lambert (Surgery 1997). Briefly, MDA-MB-231 cells were incubated overnight in serum-free medium supplemented with ITS liquid supplement (Sigma) with different concentrations of compound (1, 10, 17.5, 25 and 50 μM). Supematant was collected and concentrated with Ultrafree 30 kDA (Millipore). Equal amount of proteins, as determined by Bradford measurement, were loaded onto a 10% w/v polyacrylamide gel containing 1% gelatin and 0.1% SDS (Novex). After electrophoresis, gels were washed in Novex Zymogram Renaturing buffer for 30 min at room temperature and incubated overnight at 37° C. in Novex Zymogram developing buffer. Gels were stained in Coomassie Brilliant Blue G-250, and the gelatinolytic activity was visualized as a clear band against the blue background of the stained gelatin.

f) Cytoskeleton Analysis

Since major rearrangements of cytoskeleton are observed in tumor cells and since the small GTPases are known to regulate these events, analysis of actin cytoskeleton was performed. Subconfluent cells seeded onto coverslips were treated with different concentration of compound (1, 10, 17.5, 25 and 50 μM) or vehicle for 24 h, before being fixed in 4% formaldehyde for 15 min., permeabilized in 0.2% Triton X100 for 5 minutes and incubated in PowerBlock (Biogenex) for 10 min. Actin filaments were stained with 0.5 μg/ml fluorescein isothiocyanate (FITC)-labelled phalloidin for 1 hour. Analysis was performed using an inverted fluorescent microscope.

Results

The compounds were tested through the different in vitro tests described above. Results are presented in Table 1.

TABLE I

| | Screening Results | | | | | | | | |
|---|---|---|---|---|---|---|---|---|---|
| | Toxicity 6d (IC 50, μM) | | | | | | Anchorage-independent | | |
| | H460 | HCT116 | MDA231 | MCF7 | NIH3T3 | MRC-5 | MCF10-A | Growth (IC50) | Invasion |
| EH6600 | >50 | >50 | >25 | 30 | ND | ND | ND | — | ND |
| EH15700 | >50 | >50 | 20 | >50 | ND | ND | ND | — | ND |
| EH17600 | >50 | >50 | >25 | 17.5 | ND | ND | ND | ND | ND |
| EH20700 | >50 | >50 | >50 | >50 | ND | ND | ND | ND | ND |
| EH27900 | >50 | >50 | >25 | 40 | ND | ND | ND | ND | ND |
| EH26900 | >50 | >50 | >50 | >50 | ND | ND | ND | ND | ND |
| EH15301 | >50 | >50 | >50 | >50 | >50 | ND | ND | ND | ND |
| EH17401 | >50 | >50 | >50 | >50 | >50 | ND | ND | ND | ND |

TABLE I-continued

Screening Results

| | | | | | | | | | |
|---|---|---|---|---|---|---|---|---|---|
| EH18401 | >50 | >50 | >50 | >50 | >50 | ND | ND | ND | ND |
| EH22501 | >50 | >50 | 50 | >50 | >50 | ND | ND | ND | ND |
| EH10501 | >50 | >50 | >50 | >50 | >50 | ND | ND | ND | ND |
| EH26101 | 35 | >50 | 40–45 | >50 | 1–5 | ND | ND | 50 μM | ND |
| EH30101 | 35 | 50 | 30–35 | 45 | 0.1–0.5 | ND | ND | 7.5 μM | ND |
| EH16201 | 20 | 50 | >50 | 25 | 25 | ND | ND | 12.5 μM | ND |
| EH17700 | 15 | 30 | 15–20 | 20 | ND | >50 | ND | — | ND |
| EH5500 | 15 | 50 | >50 | 35 | ND | ND | ND | — | ND |
| EH15500 | 35 | 50 | 15 | >50 | ND | ND | ND | — | ND |
| EH10600 | 25 | >50 | 10 | 40 | ND | ND | ND | — | ND |
| EH22900 | 15 | 10 | 30 | 50 | 30 | 25 | >50 | <<1 μM | Decrease |
| EH18900 | 40 | 35 | >50 | 30 | 0.5 | 17.5 | 50 | 1–5 μM | Increase |
| EH31101 | 25 | 30 | 25 | 25 | >50 | ND | 35 | <1 μM | Increase |
| EH9301 | 25 | 20 | 25 | 20 | 50 | 35 | >50 | — | No effect |
| EH16701 | 7 | 8.5 | 47.5 | 15 | >50 | >50 | >50 | — | No effect |
| EH17701 | 5–10 | 5–10 | 35 | 15 | ND | 17.5 | >50 | | |
| EH18601 | 25 | 50 | >50 | 15 | >50 | ND | ND | — | No effect |
| EH30701 | 15 | 8 | 15 | 20 | ND | ND | ND | — | Decrease |
| EH28900 | 10 | 25 | 5 | 20 | 0.5 | ND | 50 | — | ND |
| EH7701 | 6 | 7.5 | 22.5 | 17.5 | 40 | 20 | >50 | — | No effect |

| | Small GTPases | | Colony formation | phase contrast | Cell architecture modification | | | | Migration |
|---|---|---|---|---|---|---|---|---|---|
| | | | | | actin staining (R: ruffles; FC: focal complexes) | | | | |
| | Ras | Rac | | | NIH3T3 | MDA231 | H460 | HCT116 | ND |
| EH5500 | — | — | - | + | cell destructuration | ND | ND | ND | ND |
| EH15500 | — | ND | - | + | cell destructuration | ND | ND | ND | ND |
| EH17700 | — | — | - | - | ND | ND | ND | ND | no effect |
| EH10600 | — | — | - | + | cell destructuration | ND | ND | ND | ND |
| EH22900 | — | — | + | + | R-, FC+ | cell spreading | ND | ND | inhibition |
| EH18900 | — | ND | + | + | R-, FC+ | — | cell spreading | cell spreading | no effect |
| EH31101 | — | — | - | + | R-, FC+ | — | — | — | no effect |
| EH9301 | ND | ND | - | - | ND | ND | ND | ND | no effect |
| EH16701 | ND | ND | ND | - | ND | cell spreading | ND | ND | ND |
| EH17701 | ND | ND | ND | - | ND | cell spreading | ND | ND | ND |
| EH18601 | ND | ND | ND | - | ND | ND | ND | ND | ND |
| EH30701 | ND | ND | ND | - | ND | cell spreading | ND | ND | ND |
| EH28900 | — | ND | ND | - | ND | ND | ND | ND | ND |
| EH7701 | ND | ND | ND | - | ND | cell spreading | ND | ND | ND |

ND: Not Determined; –: no effect of the compound was observed; +: an effect of the compound was observed. Toxicity test: the sign > was used when the IC50 was not reached at the highest concentration of compound tested. Anchorage-independent growth test: a sign – was used when no difference was observed between the IC50 in 3-dimensional growth conditions and regular growth conditions (HCT116 cells in anchorage independent growth assay versus HCT116 in toxicity assay). Cell architecture: a decrease in cellular ruffles density was noted R–, an increase in focal complexes density was noted FC+. General observations are also indicated The compounds can be schematically divided into two groups, one with an alcohol, or a benzyloxymethyl group in position R, and one with an acidic or a benzylcarbamoyl group at the same position. Cytotoxicity tests showed that the first group of compounds were the most toxic on tumoral cell lines. Nine compounds were toxic on at least three of the four tumoral cell lines with IC50 after 6 days of treatment inferior to 30 μM. Compounds EH16701, EH7701, EH17701, EH30701, EH22900 and EH28900 were the most toxic with an IC 50 inferior or equal to 15 μM on HCT116 after 6 days of treatment. The two compounds EH22900 and EH18900 inhibited Ras-dependent neoR clones formation (the effect of EH16701, EH7701, EH17701 and EH30701 have not been tested yet in this assay). Results are shown for compound EH22900 on FIG. 1.

Compound EH22900 also showed the strongest effect on anchorage-independent growth (FIG. 2). Compound EH31101 also showed a significant, although less severe, effect on anchorage-independent growth.

Whereas compounds EH5500, EH15500 and EH10600 affected the general morphology of NIH3T3 cells, as detected by β-actin staining, a specific inhibition of membrane ruffles and an increase in the number of stress fibers was observed in the case of compounds EH22900, EH18900 and EH31101, at a concentration of 10 μM, 10 μM and 50 μM respectively. Results are shown for compound EH22900 in FIG. 3. Compound EH22900 also increased MDA-MB-231 spreading.

Concerning compound EH31101, a dose-dependant increase in spreading and a disruption of cell-to-cell junctions was observed in the presence of 25 μM and 10 μM of compound EH31101, on H460 and HCT116 tumor cells, respectively.

An in vitro evaluation of the effect of compounds EH22900, EH18900, EH17701, EH16701, EH30701, EH18601, EH7701, EH9301 and EH31101 on invasive properties of MDA-MB-231 cells showed a significant inhibition with compounds EH22900, EH17701 and EH30701 at a concentration of 17.5 μM. An increase in invasive properties was noted for compounds EH18900 and EH31101 at 50 μM and 10 μM, respectively. No significant effect on invasion was observed with either other compound. Results are presented for compound EH22900 on FIG. 4.

Inhibition of serum-induced migration was observed at 25 μM for compound EH22900 and at 10 μM for compound EH31101. Results are presented for compound EH22900 on FIG. 5.

Finally, the ability of tumor cells to secrete the metalloproteases MMP-2 and MMP-9 in the presence of compound EH22900 or EH31101 was quantified by a zymogram gel. Compounds EH22900 and EH31100 inhibited MMP-2 and MMP-9 in a dose-dependant manner at concentrations of 5 μM and 0.1 μM, respectively.

These results thus illustrate the ability of the compounds of this invention (and the particular efficacy of compounds EH22900, EH30701 and EH17701) to inhibit growth of tumor cells, to affect actin architecture and specific characteristics of tumor cells such as anchorage-independent growth and invasion.

What is claimed is:

1. A compound having a general formula (I):

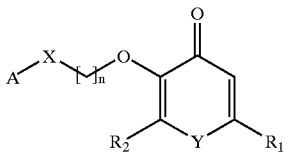

wherein:

$R_1$ is $CH_2R_3$ or $COR_3$;

$R_2$ represents a hydrogen atom or an alkenyl group containing from 3 to 6 carbon atoms;

$R_3$ is —OH, —$OR_4$, —$SR_4$, —$NR_5R_6$, or

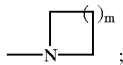

$R_4$ represents a group selected from alkyl containing from 1 to 6 carbon atoms, aryl, aralkyl, alkanoyl from 2 to 6 carbon atoms and arylcarbonyl;

$R_5$ and $R_6$, independently from each other, are selected from a hydrogen atom, an alkyl group having from 1 to 10 carbon atoms, an aryl and an aralkyl;

m is 2 or 3;

n represents an integer between 1 and 10 inclusive;

X represents an oxygen atom, a sulfur atom or a radical —$NR_7$—;

Y represents an oxygen atom;

$R_7$, identical or different, is selected in a group consisting of a hydrogen atom, an alkyl group having from 1 to 10 carbon atoms, an aryl and an aralkyl;

A represents either a substituted phenyl group of formula

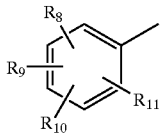

in which:

$R_8$, $R_9$, $R_{10}$ and $R_{11}$, independently from each other, are selected from a hydrogen atom, a halogen atom (preferably F, Cl, or Br), a hydroxyl group, a $(C_1-C_{10})$alkyl group, an $(C_1-C_{10})$alkanoyl group, a $(C_1-C_{10})$alkoxy group, an aryl group, an aralkyl group, an arylcarbonyl group, a mono- or poly-cyclic hydrocarbon group, —$NO_2$, —CN, a —$NR_{12}R_{13}$ group or a trifluoro$(C_1-C_6)$alkyl group; $R_8$, $R_9$, $R_{10}$ and $R_{11}$, not being simultaneously hydrogen atom, or alternatively two substituents, $R_8$ and $R_9$, may form together a mono- or poly-cyclic hydrocarbon group with the carbon atoms of the phenyl group they are attached and the two other substituents, $R_{10}$ and $R_{11}$, are as defined above;

or A represents a 5- or 6-membered heterocyclic ring which has 1 to 3 hetero-atoms selected from oxygen, sulfur and nitrogen, said ring is bonded directly to X;

$R_{12}$ and $R_{13}$, independently from each other, are selected in the group consisting of a hydrogen atom, an alkyl group having from 1 to 10 carbon atoms, an aryl and an aralkyl;

with the provisos that:

when X is an oxygen atom, $R_2$ is a hydrogen atom, n is 5 and $R_8$ on the ortho position on the phenyl group is n-propyl group, then $R_9$, $R_{10}$ and $R_{11}$ are different from hydrogen;

when X is an oxygen atom, $R_2$ is a hydrogen atom, n is 5, $R_8$ on the ortho position on the phenyl group is n-propyl group, $R_9$ on the meta position is an hydroxyl group, and $R_{10}$ on the para position is an acetyl group; then $R_{11}$ is different from hydrogen;

when X is an oxygen atom, $R_2$ is a hydrogen atom, n is 2 or 3, then A is different from a non-substituted naphthalene group;

its optical isomers, geometrical isomers, salt, or hydrates thereof.

2. A compound according to claim 1, wherein X is oxygen.

3. A compound according to claim 1, wherein n is from 4 to 7 inclusive.

4. A compound according to claim 1, wherein $R_1$ is —$CH_2OH$, —$CH_2$—O-benzyl, —$CO_2H$ or —CO—NH-benzyl.

5. A compound according to claim 1, wherein $R_2$ is a hydrogen atom or a propen-1-yl group.

6. A compound according to claim 1, wherein A is a substituted phenyl.

7. A compound according to claim 1, wherein A is a phenyl substituted by at least one halogen atom, preferably chlorine.

8. A compound according to claim 7, wherein two substituents simultaneously represent Cl.

9. A compound according to the claim 1, wherein A is a substituted phenyl, $R_8$ represents a hydrogen atom, a propyl group or an ethoxy group, $R_9$ and $R_{10}$ represent a hydrogen atom, or an halogen atom, preferably chlorine, and $R_{11}$ is a hydrogen atom.

10. A compound according to claim 1, which is chosen in the group consisting of:

5-[5-(4-Chlorophenyloxy)pentyloxy]-2-(hydroxymethyl)-4H-pyran-4-one
5-[5-(3-Chlorophenyloxy)pentyloxy]-2-(hydroxymethyl)-4H-pyran-4-one
5-[5-(3,4-Dichlorophenyloxy)pentyloxy]-2-(hydroxymethyl)-4H-pyran-4-one
5-[4-(3,4-Dichlorophenyloxy)butyloxy]-2-(hydroxymethyl)-4H-pyran-4-one
5-[5-(3,4-Dichloro-2-proylphenyloxy)pentyoxy]-2-(hydroxymethyl)-4H-pyran-4-one 5-[5-(4,5-Dichloro-2-proylphenyloxy)pentyoxy]-2-(hydroxymethyl)-4H-pyran-4-one 5-[5-(2-Ethyloxyphenyloxy)pentyloxy]-2-(hydroxymethyl)-4H-pyran-4-one 5-[6-(3,4-Dichloro-2-propylphenyloxy)hexyloxy]-2-(hydroxymethyl)-4H-pyran-4-one 5-[7-(3,4-Dichloro-2-propylphenyloxy)heptyloxy]-2-(hydroxymethyl)-4H-pyran-4-one 5-[9-(3,4-Dichlorophenyloxy)nonyloxy]-2-(hydroxymethyl)-4H-pyran-4-one 2-(Benzyloxymethyl)-5-[5-(3,4-dichlorophenyloxy)pentyloxy]-2-(hydroxymethyl)-4H-pyran-4-one 5-[5-(4-Chlorophenyloxy)pentyloxy]-4-oxo-4H-pyran-2-carboxylic acid 5-[5-(3-Chlorophenyloxy)pentyloxy]-4-oxo-4H-pyran-2-carboxylic acid 5-[5-(3,4-Dichlorophenyloxy)pentyloxy]-4-oxo-4H-pyran-2-carboxylic acid 5-[4-(3,4-Dichlorophenyloxy)butyloxy]-4-oxo-4H-pyran-2-carboxylic acid 5-[5-(3,4-Dichloro-2-propylphenyloxy)pentyloxy]-4-oxo-4H-pyran-2-carboxylic acid 5-[5-(2-Ethyloxyphenyloxy)pentyloxy]-4-oxo-4H-pyran-2-carboxylic acid N-Benzyl-5-[5-(4-chlorophenyloxy)pentyloxy]-4-oxo-4H-pyran-2-carboxamide (E)-3-[5-(4-Chlorophenyloxy)pentyloxy]-6-(hydroxymethyl)-2-(propen-1-yl)-4H-pyran-4-one (E)-3-[5-(3-Chlorophenyloxy)pentyloxy]-6-(hydroxymethyl)-2-(propen-1-yl)-4H-pyran-4-one (E)-3-[5-(3,4-Chlorophenyloxy)pentyloxy]-6-(hydroxymethyl)-2-(propen-1-yl)-4H-pyran-4-one (E)-3-[5-(3,4-Chloro-2-propylphenyloxy)pentyloxy]-6-(hydroxymethyl)-2-(propen-1-yl)-4H-pyran-4-one (E)-6-(Hydroxymethyl)-2-(propen-1-yl)-3-[5-(2-propylphenyloxy)pentyloxy]-4H-pyran-4-one (E)-3-[5-(4-Chlorophenyloxy)pentyloxy]-2-(propen-1-yl)-4-oxo-4H-pyran-6-carboxylic acid (E)-3-[5-(3-Chlorophenyloxy)pentyloxy]-2-(propen-1-yl)-4-oxo-4H-pyran-6-carboxylic acid (E)-3-[5-(3,4-Dichlorophenyloxy)pentyloxy]-2-(propen-1-yl)-4-oxo-4H-pyran-6-carboxylic acid (E)-3-[5-(3,4-Dichloro-2-propylphenyloxy)pentyloxy]-2-(propen-1-yl)-4-oxo-4H-pyran-6-carboxylic acid (E)-2-(Propen-1-yl)-3-[5-(2-propylphenyloxy)pentyloxy]-4-oxo-4H-pyran-6-carboxylic acid.

11. A compound according to claim 1, which is 5-[5-(3,4-dichloro-2-propylphenyloxy)pentyloxy]-2-(hydroxymethyl)-4H-pyran-4-one.

12. A pharmaceutical composition comprising at least one compound according to claim 1 and a pharmaceutically acceptable vehicle or carrier.

13. A method for the treatment of a disease associated with abnormal cell proliferation, comprising administering to a patient in need of such treatment a therapeutically effective amount of at least one compound of general formula (I) as disclosed in claim 1, wherein:

$R_1$ is $CH_2R_3$ or $COR_3$;

$R_2$ represents a hydrogen atom or an alkenyl group containing from 3 to 6 carbon atoms;

$R_3$ is —OH, —OR$_4$, —SR$_4$, —NR$_5$R$_6$, or

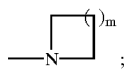

$R_4$ represents a group selected from alkyl containing from 1 to 6 carbon atoms, aryl, aralkyl, alkanoyl from 2 to 6 carbon atoms and arylcarbonyl;

$R_5$ and $R_6$, independently from each other, are selected from a hydrogen atom, an alkyl group having from 1 to 10 carbon atoms, an aryl and an aralkyl;

m is 2 or 3;

n represents an integer between 1 and 10 inclusive;

X represents an oxygen atom, a sulfur atom or a radical —NR$_7$—;

Y represents an oxygen atom;

$R_7$, identical or different, is selected in a group consisting of a hydrogen atom, an alkyl group having from 1 to 10 carbon atoms, an aryl and an aralkyl;

A represents either a substituted phenyl group of formula

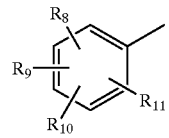

in which:

$R_8$, $R_9$, $R_{10}$ and $R_{11}$, independently from each other, are selected from a hydrogen atom, a halogen atom (preferably F, Cl, or Br), a hydroxyl group, a $(C_1-C_{10})$alkyl group, an $(C_1-C_{10})$alkanoyl group, a $(C_1-C_{10})$alkoxy group, an aryl group, an aralkyl group, an arylcarbonyl group, a mono- or poly-cyclic hydrocarbon group, —NO$_2$, —CN, a —NR$_{12}$R$_{13}$ group or a trifluoro($C_1-C_6$)alkyl group; $R_8$, $R_9$, $R_{10}$ and $R_{11}$, not being simultaneously hydrogen atom, or alternatively two substituents, $R_8$ and $R_9$, may form together a mono- or poly-cyclic hydrocarbon group with the carbon atoms of the phenyl group they are attached and the two other substituents, $R_{10}$ and $R_{11}$, are as defined above;

or alternatively two substituents may form together a mono- or poly-cyclic hydrocarbon group with the carbon atoms of the phenyl group they are attached and $R_8$ is as defined above;

or A represents a 5- or 6-membered heterocyclic ring which has 1 to 3 hetero-atoms selected from oxygen, sulfur and nitrogen, said ring is bonded directly to X;

$R_{12}$ and $R_{13}$, independently from each other, are selected in the group consisting of a hydrogen atom, an alkyl group having from 1 to 10 carbon atoms, an aryl and an aralkyl;

its optical isomers, geometrical isomers, salt, or hydrates thereof.

14. A method according to claim 13, by administering a compound of formula (I) wherein:

X is oxygen; and/or n is from 4 to 7 inclusive; and/or $R_1$ is —CH$_2$OH, —CH$_2$—O-benzyl, —CO$_2$H or —CO—NH-benzyl; and/or $R_2$ is a hydrogen atom or a propen-1-yl group; and/or A is a substituted phenyl.

15. A method according to claim 13, wherein the compound of formula (I) is one wherein A is a phenyl substituted by at least one halogen atom, preferably chlorine.

16. A method according to claim 13, wherein the compound of formula (I) corresponds to one wherein A is a 3,4-dichlorophenyl moiety.

17. A method according to claim 13, of a compound of formula (I) wherein A is a substituted phenyl, $R_8$ represents a hydrogen atom, a propyl group or an ethoxy to group, $R_9$ and $R_{10}$ represent a hydrogen atom, or an halogen atom, preferably chlorine, and $R_{11}$ is a hydrogen atom.

18. A method according to claim 13, wherein the compound is chosen in the group consisting of:

5-[5-(4-Chlorophenyloxy)pentyloxy]-2-(hydroxymethyl)-4H-pyran-4-one
5-[5-(3-Chlorophenyloxy)pentyloxy]-2-(hydroxymethyl)-4H-pyran-4-one
5-[5-(3,4-Dichlorophenyloxy)pentyloxy]-2-(hydroxymethyl)-4H-pyran-4-one
5-[4-(3,4-Dichlorophenyloxy)butyloxy]-2-(hydroxymethyl)-4H-pyran-4-one
5-[5-(3,4-Dichloro-2-propylphenyloxy)pentyloxy]-2-(hydroxymethyl)-4H-pyran-4-one
5-[5-(4,5-Dichloro-2-propylphenyloxy)pentyloxy]-2-(hydroxymethyl)-4H-pyran-4-one
5-[5-(2-Ethyloxyphenyloxy)pentyloxy]-2-(hydroxymethyl)-4H-pyran-4-one
5-[6-(3,4-Dichloro-2-propylphenyloxy)hexyloxy]-2-(hydroxymethyl)-4H-pyran-4-one
5-[7-(3,4-Dichloro-2-propylphenyloxy)heptyloxy]-2-(hydroxymethyl)-4H-pyran-4-one
5-[9-(3,4-Dichlorophenyloxy)nonyloxy]-2-(hydroxymethyl)-4H-pyran-4-one
2-(Benzyloxymethyl)-5-[5-(3,4-dichlorophenyloxy)pentyloxy]-2-(hydroxymethyl)-4H-pyran-4-one
5-[5-(4-Chlorophenyloxy)pentyloxy]-4-oxo-4H-pyran-2-carboxylic acid
5-[5-(3-Chlorophenyloxy)pentyloxy]-4-oxo-4H-pyran-2-carboxylic acid
5-[5-(3,4-Dichlorophenyloxy)pentyloxy]-4-oxo-4H-pyran-2-carboxylic acid
5-[4-(3,4-Dichlorophenyloxy)butyloxy]-4-oxo-4H-pyran-2-carboxylic acid
5-[5-(3,4-Dichloro-2-propylphenyloxy)pentyloxy]-4-oxo-4H-pyran-2-carboxylic acid
5-[5-(2-Ethyloxyphenyloxy)pentyloxy]-4-oxo-4H-pyran-2-carboxylic acid
N-Benzyl-5-[5-(4-chlorophenyloxy)pentyloxy]-4-oxo-4H-pyran-2-carboxamide
(E)-3-[5-(4-Chlorophenyloxy)pentyloxy]-6-(hydroxymethyl)-2-(propen-1-yl)-4H-pyran-4-one
(E)-3-[5-(3-Chlorophenyloxy)pentyloxy]-6-(hydroxymethyl)-2-(propen-1-yl)-4H-pyran-4-one
(E)-3-[5-(3,4-Chlorophenyloxy)pentyloxy]-6-(hydroxymethyl)-2-(propen-1-yl)-4H-pyran-4-one
(E)-3-[5-(3,4-Chloro-2-propylphenyloxy)pentyloxy]-6-(hydroxymethyl)-2-(propen-1-yl)-4H-pyran-4-one
(E)-6-(Hydroxymethyl)-2-(propen-1-yl)-3-[5-(2-propylphenyloxy)pentyloxy]-4H-pyran-4-one
(E)-3-[5-(4-Chlorophenyloxy)pentyloxy]-2-(propen-1-yl)-4-oxo-4H-pyran-6-carboxylic acid
(E)-3-[5-(3-Chlorophenyloxy)pentyloxy]-2-(propen-1-yl)-4-oxo-4H-pyran-6-carboxylic acid
(E)-3-[5-(3,4-Dichlorophenyloxy)pentyloxy]-2-(propen-1-yl)-4-oxo-4H-pyran-6-carboxylic acid
(E)-3-[5-(3,4-Dichloro-2-propylphenyloxy)pentyloxy]-2-(propen-1-yl)-4-oxo-4H-pyran-6-carboxylic acid
(E)-2-(Propen-1-yl)-3-[5-(2-propylphenyloxy)pentyloxy]-4-oxo-4H-pyran-6-carboxylic acid.

19. A method according to claim 13, wherein the compound is 5-[5-(3,4-dichloro-2-propylphenyloxy)pentyloxy]-2-(hydroxymethyl)-4H-pyran-4-one.

20. A method according to claim 13, for the treatment of cancers linked to oncogenic properties of GTPases.

21. A method according to claim 13, for the treatment of cancers selected from prostate cancer, ovarian cancer, pancreas cancer, lung cancer, breast cancer, liver cancer, head and neck cancer, colon cancer, bladder cancer, non-Hodgkin's lymphoma cancer and melanoma.

22. A method according to claim 13, for reducing cancer cell proliferation in a patient having cancer linked to oncogenic properties of GPTases.

23. A method according to claim 13, for treating metastatic cancers linked to oncogenic properties of GTPases in a patient.

* * * * *